US006663613B1

(12) United States Patent
Evans et al.

(10) Patent No.: US 6,663,613 B1
(45) Date of Patent: Dec. 16, 2003

(54) SYSTEM AND METHODS FOR CLOT DISSOLUTION

(75) Inventors: Michael A. Evans, Palo Alto, CA (US); Denise M. Demarais, San Jose, CA (US); Christian S. Eversull, Palo Alto, CA (US); Stephen A. Leeflang, Stanford, CA (US)

(73) Assignee: Bacchus Vascular, Inc., Santa Clara, CA (US)

(*) Notice: Subject to any disclaimer, the term of this patent is extended or adjusted under 35 U.S.C. 154(b) by 0 days.

(21) Appl. No.: 09/491,401

(22) Filed: Jan. 25, 2000

(51) Int. Cl.[7] ............................................. A61M 25/00
(52) U.S. Cl. .................... 604/523; 604/264; 604/35; 604/95.01; 604/96.01; 604/101.01; 604/101.03; 604/101.04
(58) Field of Search ........................... 604/264, 19, 35, 604/36, 48, 22, 95.01–95.05, 96.01, 97.01, 97.02, 101.01, 101.03, 101.04, 101.05, 164.13, 266–268, 523, 528; 606/192, 194, 167, 170, 180, 200, 159, 171; 600/570, 571, 585, 115, 116, 137, 139, 143

(56) References Cited

U.S. PATENT DOCUMENTS

| | | | |
|---|---|---|---|
| 4,425,908 A | * | 1/1984 | Simon ........................ 128/899 |
| 4,445,509 A | | 5/1984 | Auth |
| 4,573,966 A | | 3/1986 | Weikl et al. |
| 4,646,736 A | | 3/1987 | Auth |
| 4,794,928 A | | 1/1989 | Kletschka |
| 4,923,462 A | | 5/1990 | Stevens |
| 5,041,093 A | | 8/1991 | Chu |
| 5,059,178 A | | 10/1991 | Ya |
| 5,067,957 A | | 11/1991 | Jervis |
| 5,116,352 A | | 5/1992 | Schnepp-Pesch et al. |
| 5,135,484 A | | 8/1992 | Wright |
| 5,163,905 A | | 11/1992 | Don Michael |
| 5,176,693 A | | 1/1993 | Pannek, Jr. |
| 5,190,546 A | | 3/1993 | Jervis |

(List continued on next page.)

FOREIGN PATENT DOCUMENTS

| | | |
|---|---|---|
| WO | WO 96/01591 | 1/1996 |
| WO | WO 97/11738 | 4/1997 |
| WO | WO 99/04701 | 2/1999 |
| WO | WO 99/23952 | 5/1999 |
| WO | WO 00/41762 | 7/2000 |

OTHER PUBLICATIONS

Bildsoe et al., "Mechanical clot dissolution: new concept," *Radiology*, vol. 171, No. 1, pp. 231–233 (Apr. 1989).

Kandarpa et al., "Forceful pulsatile local infusion of enzyme accelerates thrombolysis: In vivo evaluation of a new delivery system," *Radiology*, vol. 168, No. 3, pp. 739–744 (Sep. 1988).

LeVeen et al., "Accelerated thrombolysis by vibration," *University of Nebraska Medical Center & Veterans Affairs Medical Center, Omaha, Nebraska*, 4 pages.

Ritchie et al., "Mechanical thrombolysis: a new rotational catheter approach for acute thrombi," *Circulation*, vol. 3, No. 5, pp. 1006–1012 (May 1986).

Tachibana, K., "Enhancement of fibrinolysis with ultrasound energy," *Journal of vascular and interventional radiology*, vol. 3, No. 2, pp. 299–303 (May 1992).

Primary Examiner—Brian L. Casler
Assistant Examiner—Cris Rodriguez
(74) Attorney, Agent, or Firm—Townsend and Townsend and Crew LLP

(57) ABSTRACT

Clot disruption and dissolution are achieved using a catheter having both an agitator and the ability to deliver a thrombolytic agent. The catheter is introduced to a target region with a blood vessel and the agitator manipulated to engage and disrupt a region of clot therein. The thrombolytic agent, such as tPA, streptokinase, or urokinase, is directly released into the clot at the point where the agitator is engaging the clot. In this way, the thrombolytic activity of the agent is enhanced and the dissolution of the clot is improved.

26 Claims, 17 Drawing Sheets

U.S. PATENT DOCUMENTS

| | | | |
|---|---|---|---|
| 5,222,941 A | | 6/1993 | Don Michael |
| 5,279,546 A | | 1/1994 | Mische et al. |
| 5,284,486 A | | 2/1994 | Kotula et al. |
| 5,312,427 A | | 5/1994 | Shturman |
| 5,330,484 A | | 7/1994 | Günther et al. |
| 5,356,418 A | | 10/1994 | Shturman |
| 5,360,432 A | | 11/1994 | Shturman |
| 5,370,653 A | * | 12/1994 | Cragg ............... 600/569 |
| 5,380,273 A | | 1/1995 | Dubrul et al. |
| 5,410,093 A | | 4/1995 | Dorai |
| 5,417,703 A | * | 5/1995 | Brown et al. ............ 606/159 |
| 5,419,774 A | * | 5/1995 | Willard et al. ............ 604/22 |
| 5,462,529 A | | 10/1995 | Simpson et al. |
| 5,490,859 A | | 2/1996 | Mische et al. |
| 5,498,236 A | | 3/1996 | Dubrul et al. |
| 5,501,694 A | | 3/1996 | Ressemann et al. |
| 5,507,795 A | * | 4/1996 | Chiang et al. ............ 606/167 |
| 5,540,707 A | | 7/1996 | Ressemann et al. |
| 5,549,119 A | | 8/1996 | Solar |
| 5,554,114 A | | 9/1996 | Wallace et al. |
| 5,554,163 A | * | 9/1996 | Shturman ............... 604/22 |
| 5,556,408 A | | 9/1996 | Farhat |
| 5,569,275 A | * | 10/1996 | Kotula et al. ............ 606/159 |
| 5,584,843 A | * | 12/1996 | Wulfman et al. ............ 604/22 |
| 5,643,228 A | | 7/1997 | Schucart et al. |
| 5,674,198 A | | 10/1997 | Leone |
| 5,709,874 A | | 1/1998 | Hanson et al. |
| 5,713,848 A | | 2/1998 | Dubrul et al. |
| 5,758,656 A | | 6/1998 | Schroeder |
| 5,766,191 A | | 6/1998 | Trerotola |
| 5,795,322 A | | 8/1998 | Boudewijn |
| 5,836,868 A | | 11/1998 | Ressemann et al. |
| 5,843,103 A | | 12/1998 | Wulfman |
| 5,873,882 A | | 2/1999 | Straub et al. |
| 5,876,414 A | | 3/1999 | Straub |
| 5,897,567 A | | 4/1999 | Ressemann et al. |
| 5,904,698 A | | 5/1999 | Thomas et al. |
| 5,908,395 A | | 6/1999 | Stalker et al. |
| 5,928,203 A | | 7/1999 | Davey et al. |
| 5,947,985 A | | 9/1999 | Imran |
| 5,951,514 A | | 9/1999 | Sahota |
| 5,954,737 A | * | 9/1999 | Lee ............... 606/159 |
| 5,957,901 A | | 9/1999 | Mottola et al. |
| 5,972,019 A | | 10/1999 | Engelson et al. |
| 6,022,336 A | * | 2/2000 | Zadno-Azizi et al. .. 604/101.05 |
| 6,027,514 A | * | 2/2000 | Stine et al. ............ 600/564 |
| 6,036,708 A | | 3/2000 | Sciver |
| 6,063,069 A | * | 5/2000 | Cragg et al. ............ 604/22 |
| 6,090,118 A | * | 7/2000 | McGuckin, Jr. ............ 606/159 |
| 6,113,614 A | * | 9/2000 | Mears ............... 606/159 |
| 6,146,395 A | * | 11/2000 | Kanz et al. ............ 606/159 |
| 6,156,046 A | * | 12/2000 | Passafaro et al. ............ 128/898 |
| 6,168,579 B1 | * | 1/2001 | Tsugita ............... 604/104 |
| 6,179,816 B1 | * | 1/2001 | Mottola et al. ............ 604/264 |
| 6,295,990 B1 | * | 10/2001 | Lewis et al. ............ 128/898 |
| 6,322,572 B1 | * | 11/2001 | Lee ............... 606/159 |
| 6,383,205 B1 | * | 5/2002 | Samson et al. ............ 606/200 |

\* cited by examiner

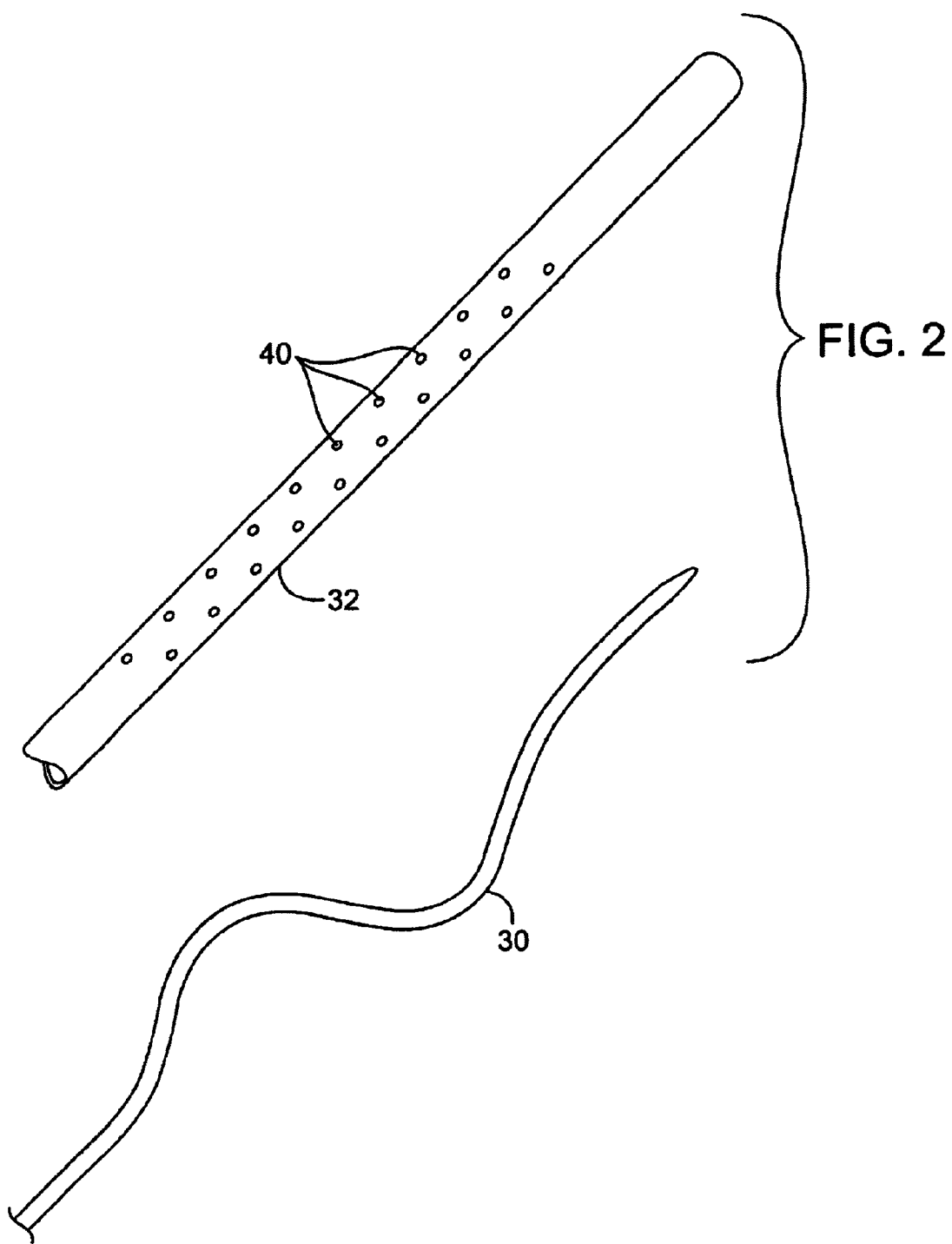

SYSTEM AND METHODS FOR CLOT DISSOLUTION

BACKGROUND OF THE INVENTION

1. Field of the Invention

The present invention relates generally to medical devices and methods. More particularly, the present invention relates to devices and methods for dissolving and disrupting occlusive materials from blood vessels.

Thrombosis and atherosclerosis are common ailments which occur in humans and which result from the deposition of thrombus within the lumens of blood vessels. When hardened, such deposits are commonly referred to as plaque. Such deposits are most common in the peripheral blood vessels that feed the limbs of the human body and the coronary arteries which feed the heart. Stasis, incompetent valves, and trauma in the venous circulation cause thrombosis, particularly occurring as a deep vein thrombosis in the peripheral vasculature. When such deposits accumulate in localized regions of the blood vessel, they can restrict blood flow and cause a serious health risk.

In addition to forming in the natural vasculature, thrombosis is a serious problem in "artificial" blood vessels, particularly in peripheral femoral-popliteal and coronary bypass grafts and dialysis access grafts and fistulas. The creation of such artificial blood vessels requires anastomotic attachment at at least one, and usually at at least two, locations in the vasculature. Such sites of an anastomotic attachment are particularly susceptible to thrombus formation due to narrowing caused by intimal hyperplasia, and thrombus formation at these sites is a frequent cause of failure of the implanted graft or fistula. The arterio-venous grafts and fistulas which are used for dialysis access are significantly compromised by thrombosis at the sites of anastomotic attachment and elsewhere. Thrombosis often occurs to such an extent that the graft needs to be replaced within a few years or, in the worst cases, a few months.

A variety of methods have been developed for treating thrombosis and atherosclerosis in the coronary and peripheral vasculature as well as in implanted grafts and fistulas. Such techniques include surgical procedures, such as coronary artery bypass grafting, and minimally invasive procedures, such as angioplasty, atherectomy, thrombectomy, thrombolysis, transmyocardial revasculaturization, and the like.

Of particular interest to the present invention, a variety of techniques have been developed for dissolving clot using thrombolytic agents, such as tissue plasminogen activator (tPA), streptokinase, urokinase, and the like. While such thrombolytic agents can be delivered systemically, the present invention is most particularly concerned with the local delivery of such agents and even more particularly concerned with the local delivery of such agents in combination with mechanical clot disruption.

Thrombolytic agents can be very effective at attacking and dissolving relatively soft clot, such as that formed in deep veins. Such agents, however, require time to act, and local delivery catheters often employ isolation balloons to provide high local concentrations of the active thrombolytic agents. Even with such enhanced concentrations, the agents can take extended periods to act, rendering the treatments lengthy and inefficient. In some instances, extensive regions of clot simply cannot be effectively treated using thrombolytic agents alone. In such cases, it has been further proposed to provide a mechanical element to disrupt the clot while the thrombolytic agents are being delivered. See, for example, U.S. Pat. No. 5,947,985 to Mir A. Imran. This patent describes a catheter having axially spaced-apart balloons for isolating a treatment region within a blood vessel. The catheter includes a port for delivering thrombolytic agent between the spaced-apart balloons and a helical wire for removing clot material from the wall to assist in aspiration. While a promising technique, this catheter is not optimized to enhance delivery and mixing of the thrombolytic agent directly into the clot being treated.

For these reasons, it would be desirable to provide improved apparatus, systems, methods, and kits for disrupting and dissolving vascular clot, particularly soft clot of the type found in deep vein thrombosis. It would be particularly desirable to provide methods and apparatus which can enhance the thrombolytic activity of thrombolytic agents delivered to the region being treated, and even more particularly enhance the direct introduction into and mixing of the thrombolytic agent within the mass of clot within the blood vessel. Such methods and apparatus should preferably both reduce the treatment times required for thrombolytic dissolution of vascular clot as well as improve the mechanical breakdown of that clot into smaller and smaller particles to facilitate removal of the dissolved clot. At least some of these objectives will be met by the inventions described hereinafter.

2. Description of the Background Art

Clot disruption catheters which combine the delivery of thrombolytic agents with mechanical disruption are described in, for example, U.S. Pat. Nos. 5,972,019 and 5,947,985. Other clot disruption catheters are described in, for example, U.S. Pat. Nos. 5,954,737; 5,795,322; 5,766,191; 5,556,408; 5,330,484, 5,279,546; 5,116,352; 5,014,093; and WO 96/01591. Catheters having axially spaced-apart isolation balloons for treating thrombus are shown in, for example, U.S. Pat. Nos. 5,947,985 and 5,279,546 and WO 97/11738. Catheters having helical and non-linear guidewires are described in U.S. Pat. Nos. 5,584,843; 5,360,432; 5,356,418; and 5,312,427. Other patents and patent publications of interest include U.S. Pat. Nos. 5,957,901; 5,951,514; 5,928,203; 5,908,395; 5,897,567; 5,843,103; 5,836,868; 5,713,848; 5,643,228; 5,569,275; 5,549,119; 5,540,707; 5,501,694; 5,498,236; 5,490,859; 5,380,273; 5,284,486; 5,176,693; 5,163,905; 4,923,462; 4,646,736; and 4,445,509; and WO 99/23952 and WO 99/04701. Publications of interest in the medical literature include LeVeen et al. (1992), American Heart Association Poster Presentation; Tachibana (1993) *JVIR S*:299–303; Kandarpa et al. (1998) Radiology 168: 739–744; Bildsoe et al. (1989) *Radiology* 171: 231–233; and Ritchie et al. (1986) *Circulation* 73: 1006–1012.

SUMMARY OF THE INVENTION

The present invention provides apparatus, systems, methods, and kits for disrupting and dissolving thrombus, also referred to as clot, present in a patient's vasculature, including both the arterial and venous vasculature. The present invention is particularly intended for treating thrombotic disease within the venous vasculature, such as thrombosis in the superficial vein, the central veins, the femoral-popliteal veins, the ilio-femoral vein, and the like. The present invention is also particularly intended for treating arterial thrombotic disease, such as thrombosis in the ilio-femoral artery, the superficial femoral artery, and the like.

The present invention is advantageous in a number of respects. In particular, the methods and apparatus of the present invention will provide improved introduction and mixing of thrombolytic agents into vascular clot, which in turn will improve the efficiency of clot dissolution, including both reducing the time required for dissolution and/or enhancing the degree to which the clot is dissolved, i.e., reducing the particle size of clot achieved at the end of treatment. The reduction of treatment time will reduce both the cost of treatment and the time during which the patient is undergoing the treatment. The improved degree of clot dissolution will reduce the danger of released emboli, which can be a serious risk to the patient. In particular, the methods and devices of the present invention will enhance the mixing of the thrombolytic agent while simultaneously increasing the surface area of the thrombus or clot which is available to the thrombolytic agent being introduced. The release of the thrombolytic agent directly at the point where the thrombus is being disrupted and the increase in available surface area together provide a very significant increase in the thrombolytic activity and consequent decrease of treatment time.

In a first aspect, apparatus according to the present invention comprises a catheter body having a proximal end and a distal end. The dimensions and materials of the catheter body will be selected according to the target site within the vasculature to be treated, i.e., the catheter will be sized to be introduced percutaneously or via a cut down to the vasculature at an entry and then be intravascularly advanced, typically over a guidewire, to the target site. Target sites in the peripheral, coronary, and cerebral vasculature will generally be approached through different access sites and will require catheters having different lengths, diameters, and flexibilites. The constructions of such catheters, however, are well-known and well-described in the patent and medical literature.

Means will be disposed near the distal end of the catheter body for both mechanically agitating clot and for distributing a thrombolytic agent within the clot. Both the mechanical agitation means and the thrombolytic agent distributing means will be effective over a predetermined length within the blood vessel. That is, the clot disruption apparatus of the present invention will be capable of both mechanically agitating the clot and concomitantly or simultaneously delivering the thrombolytic agent into the clot at the region of mechanical agitation over a predetermined length of clot in the blood vessel. The predetermined length will usually be at least 5 cm, more usually being at least 10 cm, and typically being in the range from 5 cm to 100 cm, usually from 10 cm to 50 cm. The length of thrombotic disease being treated will vary depending on the location of the disease within the vasculature. For example, deep vein thrombosis will often be disseminated over a length in the range from 5 cm to 100 cm. The apparatus and methods of the present invention will be capable of treating disease disseminated over these lengths as described in more detail below. The apparatus of the present invention need not be adapted to treat the entire length of the diseased region at once. It will often be possible and in some cases desirable to treat discrete lengths within the entire diseased region separately. Such discrete lengths can be treated successively, e.g., by axially translating the treatment device within the blood vessel being treated. Alternatively, the segments could be treated using different devices, optionally introduced from different introduction sites in the vasculature.

The mechanical agitating means on the catheter body may have a wide variety of specific configurations. Usually, the mechanical agitating means will comprise a radially expansible agitator which is rotatable and/or axially translatable relative to the catheter body. In the first embodiment, the radially expansible agitator will be self-expanding, e.g., it may comprise a resilient element which may be radially constrained to have a low profile (small diameter) and may be freed from radial constraint to have an enlarged profile (large diameter) with a non-linear geometry. Typically, radial constraint can be provided by a sleeve or sheath which may be axially advanced and retracted relative to the catheter body to cover and uncover the radially expansible agitator. In this way, the catheter can be introduced to a target site within the vasculature with the expansible agitator covered (and thus radially constrained). After the desired target site is reached, the sheath or sleeve can be axially retracted to release the radially expansible agitator so that it expands to engage the clot in the blood vessel. The agitator may then be rotated and/or axially translated to engage and disrupt the clot in combination with the release of a thrombolytic agent, as described in more detail below. Such rotation, oscillation, and/or translation will usually be accomplished using a motor drive unit operatively connected to the agitator, but could in some instances be performed manually in whole or in part.

In an alternative embodiment, the radially expansible agitator may comprise a resilient element which can be axially shortened to assume an enlarged profile having a non-linear geometry. For example, a self-expanding resilient element may be straightened (tensioned) by initially positioning a rod or stylet therein in order to lengthen the element and cause it to straighten to a low profile diameter. The agitator may then be expanded by retracting the rod or stylet to release the agitator from tension and permit the agitator to radially expand as a result of the agitator's inherent spring force. Alternatively, the agitator may be formed to have a generally, straight low profile configuration and be actively caused to radially expand by pulling on a rod or wire to cause axial shortening.

In all cases, the agitator may have a variety of specific geometries, such as a helical geometry, a spiral geometry, a serpentine geometry, a zig-zag geometry, an alternating helix geometry (i.e., two or more helical geometries in tandem where successive helixes are wound in opposite directions), and/or a variety of other random geometries. The geometries will be such that the resilient element can engage against and penetrate into the clot within a blood vessel as the resilient element is radially expanded. As the resilient element is thereafter rotated and/or axially translated, the element will then mechanically engage and disrupt the clot. By simultaneously introducing the thrombolytic agent directly to the region which is being mechanically engaged by the agitator, disruption and dissolution of the clot is significantly enhanced.

In a second specific aspect, the thrombolytic distributing means of the present invention will comprise a porous sheath or other perforate or foramenous structure which may be disposed over the radially expansible agitator. The porous sheath may be a thin fabric having a generally uniform porosity along its length. Alternatively, the sheath could be an impermeable membrane having a plurality of holes or ports formed along its length to permit the release of a thrombolytic agent. A wide variety of other perforate or porous structures will also be available. For example, the sheath could comprise a coil having a plurality of successive turns, where bending of the coil causes the turns to separate, creating spaces or apertures for the release of the thrombolytic agent. It would also be possible to form the sheath from an elastic material having pores which are generally closed but which open when the elastic material is tensioned, either by stretching (e.g., due to internal pressurization with the thrombolytic agent) or by deforming the elastic sheath material as the sheath is deformed into its non-linear geometry.

In all cases, the sheath will be able to release the thrombolytic agent along substantially the entire length of the agitator which is in contact with the clot to be disrupted. In this way, the thrombolytic agent will be released at the point of mechanical agitation, resulting in both improved distribution of the thrombolytic agent into the clot as well as improved disruption and dissolution of the clot. Usually, the porous sheath will be formed as a relatively closely fitting sleeve over the resilient element, e.g., so that the sheath assumes the same non-linear geometry as the resilient element. Alternatively, however, the sheath may be formed to have larger diameter, e.g., a diameter approaching the luminal diameter of the blood vessel being treated. In the latter case, the thrombolytic agent may be distributed over the entire region of the clot while the agitator presses the sheath into the clot to enhance introduction of the thrombolytic agent and dissolution of the clot. In both cases, the sheath may be elastic, i.e., expansible in response to pressure of thrombolytic agent, or inelastic. Alternatively, sheath could be a composite of an elastic fabric or membrane reinforced with a grid or network of elastic or inelastic ribs or other reinforcement members.

In an alternative embodiment of the second aspect of the present invention, the agitator may be configured to directly deliver the thrombolytic agent into the clot as the agitator is being driven. For example, when the agitator is in the form of a non-linear element, the element may be formed as a tube having a thrombolytic agent delivery lumen therein. The tube may then be provided with agent delivery ports and/or porous regions to permit the generally uniform release of the thrombolytic agent over the length of the element which is contact with the clot. In this way, the thrombolytic agent may be delivered directly into the clot and dissolution enhanced without the need to provide for a separate thrombolytic agent delivery sheath.

Optionally, the clot disruption and dissolution apparatus of the present invention may further comprise means for isolating at least a distal end of the catheter body to reduce blood flow through the region being treated by the catheter. For example, at least a single balloon may be provided on the catheter body distally or proximally of the agitator and thrombolytic agent distribution means on the catheter. When only a single balloon is used for isolation, it will preferably be on the side of the thrombolytic agent distribution means which is downstream from the region being treated. In this way, the isolation balloon will inhibit the loss of the thrombolytic agent as well as the release of emboli downstream. Preferably, isolation means will be provided both on the distal end proximal sides of the agitator and thrombolytic agent distributing means. Typically, the isolation means will comprise a pair of axially spaced-apart balloons disposed on the catheter body. Further optionally, one of the balloons may be disposed on a separate, telescoping portion of the catheter body in order to permit length adjustment of the region to be isolated. Alternatively, a variety of other isolation means, such as deployable flanges, malecot structures, expansible braids, and the like, could also be employed.

In the apparatus of the present invention which employ both an agitator and a sheath, the agitator may optionally be replaceable within the sheath and/or axially translatable within the sheath. Still further optionally, the sheath itself may be introduceable over a guidewire, either with or without the agitator being in place within the sheath. Thus, the apparatus may provide for the free interchangeability of two or more agitators and at least one guidewire for initially placing the sheath. It will be appreciated that such replaceability provides great adaptability of the systems of the present invention. For example, the sheath could be introduced to a treatment site within the vasculature over a conventional guidewire. After withdrawing the guidewire, a first agitator could be introduced to within the sheath and the target site treated by both agitation and release of the thrombolytic agent. It would then be possible to reposition the agitator within the sheath to treat a different region of the vasculature. Alternatively or additionally, it would be possible to remove the first agitator and replace it with a second agitator selected to better treat the region and/or to provide for a subsequent treatment step of that region.

The catheters of the present invention may optionally be provided with lumen(s) for introduction over a guidewire. For example, the catheter (or a sheath component thereof) may be introduced over a guidewire using a central lumen which also receives the agitator. Alternatively, separate guidewire lumen(s) could be provided on the sheath or elsewhere, e.g., a short guidewire lumen could be provided near the distal tip of the sheath beyond the non-linear region defined by the agitator. Such a short lumen would avoid interference with the agitator. A variety of specific designs will be available.

The apparatus of the present invention will still further be available of systems comprising at least one sheath together with two or more agitators which are removably replaceable within the sheath. Such systems allow for treatment of different diseases and different regions of the vasculature. The treating physician can either choose the initial combination which is best for a particular disease, or may begin treatment with one combination of sheath and agitator and continue treatment thereafter with another combination of sheath and agitator.

The present invention still further provides methods for disrupting and dissolving clot from target regions within a patient's vasculature. The methods comprise mechanically agitating the clot over a predetermined luminal length within a blood vessel and infusing a thrombolytic agent over most or all of the predetermined luminal length which is being mechanically agitated. In particular, the methods comprise infusing the thrombolytic agent in a distributed pattern over the treated length. By "distributed pattern," it is meant that the thrombolytic agent is not simply released into the treatment region but rather that it is introduced directly into the clot at the interface region where the clot is being mechanically agitated. For example, in the case where mechanical agitation is achieved using a non-linear element, the thrombolytic agent will be delivered at points which are distributed over the non-linear element so that they enter the clot at the "point of attack" described above in connection with the apparatus. The thrombolytic agent can be delivered using a porous sheath which is disposed over the non-linear agent in a sleeve-like manner. Alternatively, the thrombolytic agent can be delivered through a lumen within the non-linear agent and released through a plurality of ports or porous regions in the non-linear element. In both cases, the ability to deliver the thrombolytic agent directly into the clot as it is being mechanically penetrated by the element will enhance distribution of the thrombolytic agent within the clot and improve the efficiency of clot dissolution as well as decrease the particle size reduction achieved in a given period of time.

In specific aspects, the methods of the present invention are used to treat predetermined luminal lengths, typically having a length of at least 5 cm, usually at least 100 cm, and most usually in the range from 10 cm to 50 cm. When the blood vessel is a vein, the targeted regions may be selected from the group consisting of vena cava, iliac vein, femoral vein, popliteal vein, common iliac vein, external iliac vein, brachial vein, and subclavian vein. When the target blood vessel is an artery, the preferred arteries are the internal iliac artery, external iliac artery, popliteal artery, coronary arteries, superficial femoral artery, and the brachial artery.

Preferably, mechanical agitation comprises rotating and/or axially translating a radially expansible agitator within the blood vessel and against the clot. The exemplary agitators have been described above. Optionally, the mechanical and agitation and thrombolytic agent delivery may be performed within isolated regions of the vasculature, typically provided by inflating one or more balloons within the vasculature at either side of the treatment region. Most preferably, a pair of axially spaced-apart balloons will be disposed on either side of the treatment region to provide isolation, both to maintain higher thrombolytic agent concentrations within the region and to inhibit the release of thrombotic clot prior to sufficient dissolution of the clot.

The methods of the present invention allow for a wide variety of particular treatment protocols. For example, the agitator may be driven at different and/or variable speeds. Typically, the agitators will be rotated and/or oscillated at speeds in the range from 10 rpm to 20,000 rpm, preferably from 50 rpm to 5,000 rpm. The speeds may be set and/or adjusted at a wide variety of particular rotational speeds within these ranges. In some cases, the direction of the rotation can be reversed during the course of the procedure. It will further be possible to axially advance or retract the agitator, optionally within a sheath, during the course of treatment to enhance the disruption of the clot and introduction of the thrombolytic into the clot. Still further additionally, it will be possible to vary the width or diameter of the agitator during the course of treatment to enhance disruption.

The treatment methods of the present invention may optionally comprise aspiration of the disrupted clot from the treatment site. Aspiration may be accomplished using a lumen or lumens within the sheath and/or agitator to withdraw the disrupted clot. Optionally, mechanical means, such as an Archimedes screw, may be utilized to enhance the aspiration and removal of the disrupted clot.

Still further optionally, the disrupted clot and other fluid or fluidized materials within the treatment region may be recirculated to enhance breakup of the clot and activity of thrombolytic agent. For example, pairs of spaced-apart ports or apertures on the sheath may be used to draw in the material within the treatment region and expel that material at a different point within the treatment region. Such recirculation may significantly enhance the thrombolytic activity and decrease the treatment time.

As a still further option, it is possible to periodically or continuously introduce blood into the treatment region. tPA acts on plasminogen within the vasculature to breakup thrombus. If the treatment region of the present invention is isolated, it may be beneficial to introduce fresh blood containing plasma in order to enhance the activity of the thrombolytic agent, particularly tPA. Most simply, fresh blood could be introduced by periodically opening an isolation balloon which isolates the treatment region.

The methods of the present invention can rely on two or more of the treatment catheters to be used simultaneously. For example, in the treatment of arteriovenous grafts, it is possible to introduce two treatment catheters according to the present invention, each of which has a balloon or other occlusion device at its distal end, to an A–V graft at a point near its middle. By introducing the two treatment catheters in opposite directions, the graft can be isolated very close to the points at which it is anastomosed to the natural vasculature. After such isolation is achieved, the interior of the A–V graft can then be cleaned out according to the methods of the present invention, and preferably the released clot and thrombus may be withdrawn through an access sheath to the A–V graft.

The present invention still further comprises kits, including a catheter having an agitator in a thrombolytic agent delivery means. The kits will further include instructions for use according to any of the methods set forth above. In addition to the catheter and the instructions for use, the kits will usually further comprise packaging, such a box, pouch, tray, tube, bag, or the like, which holds the catheter and the instructions for use. Usually the catheter will be maintained sterilely within the package, and the instructions for use will be printed on a separate package insert or piece of paper. Alternatively, the instructions for use may be printed in whole or in part on a portion of the packaging.

DESCRIPTION OF THE SPECIFIC EMBODIMENTS

Figure 1:
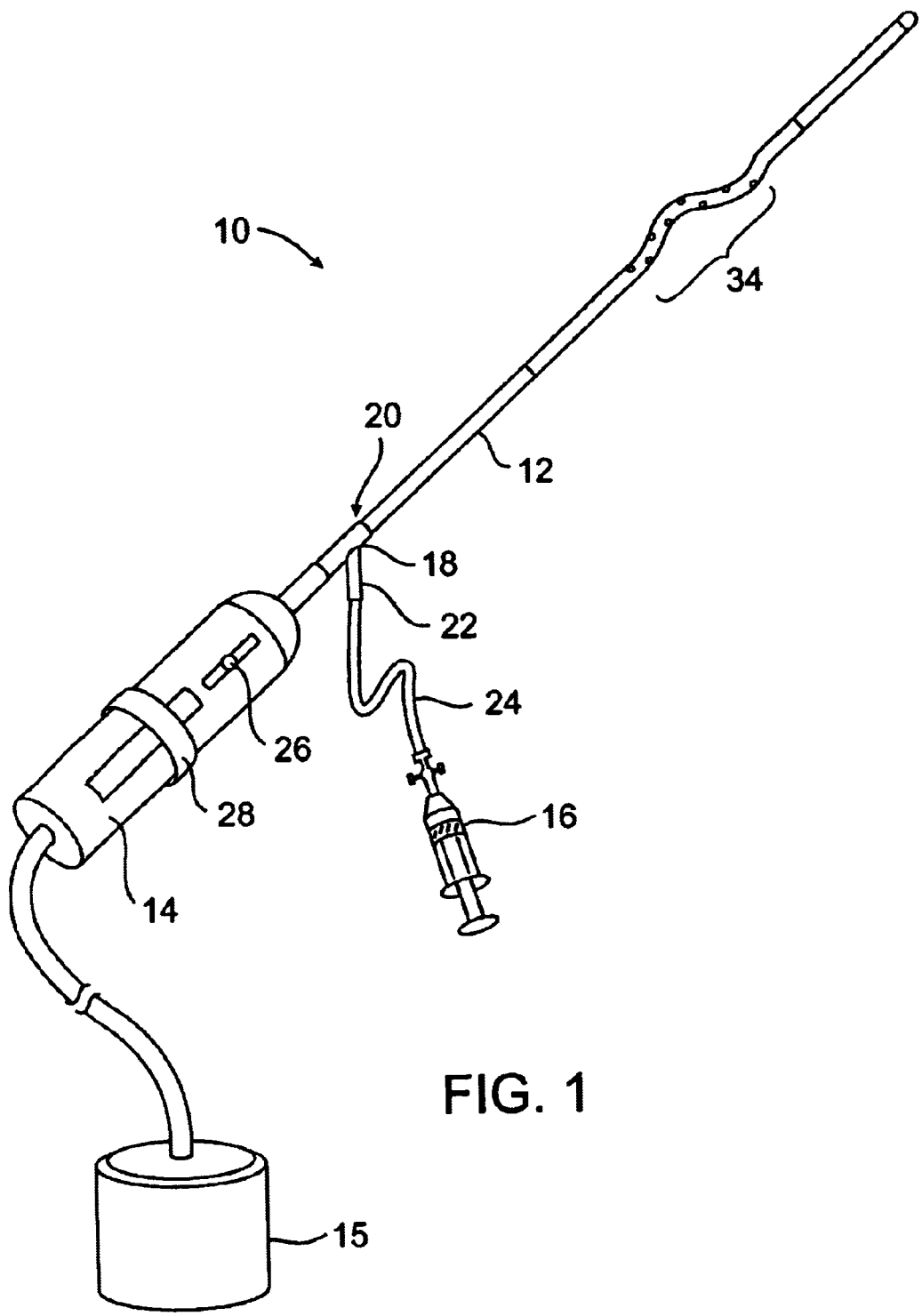
FIG. 1 is a perspective view of clot disruption apparatus constructed in accordance with the principles of the present invention.

In FIG. 1, a clot disruption apparatus 10 is shown to comprise a catheter body 12, a motor drive unit 14, and a thrombolytic agent delivery device 16. The motor drive unit 14 is attached to a hub 18 at a proximal end 20 of the catheter body 12. The thrombolytic agent delivery device is shown as a syringe which is attached to a side port 22 on hub 18 through a conventional tube 24. It will be appreciated that other thrombolytic agent delivery devices could also be used, such as pumps, gravity bags, and the like. The thrombolytic agent delivered by device 16 can be any conventional bioactive agent which is capable of disrupting and dissolving clot and thrombus, such as tissue plasminogen activator (tPA), streptokinase, urokinase, heparin, low molecular weight heparin, and the like. The thrombolytic agents may be delivered through the delivery device 16 as a bolus, continuously over time, or as combinations thereof.

Figure 2A:
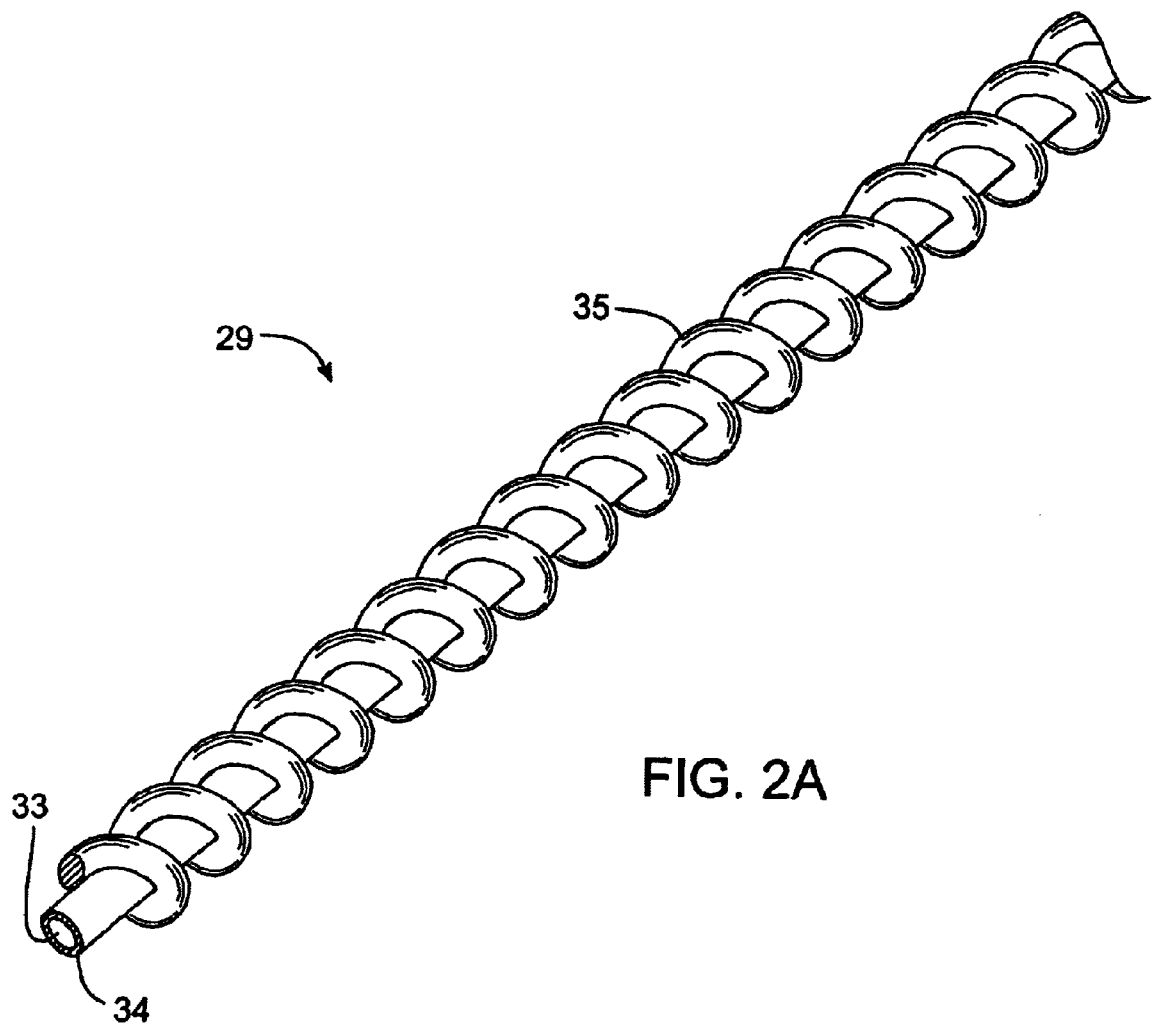
FIG. 2 is a detailed view of the distal end of the clot disruption apparatus of FIG. 1, showing the sheath and agitator components thereof.

A motor drive unit 14 includes a sliding switch 26 which controls the rotational speed of the motor and a sliding collar 28 which controls the axial position of an agitator 30 within a sheath 32 of the catheter body 12 (FIG. 2). A non-linear region 34 of the catheter body 12 is defined by the agitator 30 within the sheath 32. By axially translating the agitator 30 using the collar 28, the non-linear region of the catheter body can be moved in a proximal or distal direction along the catheter body. The motor drive unit will be capable of rotating the agitator 30 within the sheath 32 at the rotational rates set forth hereinabove. Additionally, the motor drive unit 14 may be adapted in other circumstances to oscillate the agitator, axially reciprocate the agitator, or provide for other mechanical movements of the agitator which can cause or contribute to clot disruption according to the methods of the present invention.

Referring now in particular to FIG. 2, the sheath 32 comprises a tubular body formed from a polymeric material, a fabric, or other material, and includes a plurality of fluid distribution ports 40 along its length. As illustrated, the fluid distribution ports 40 are only formed over a portion of the length of the sheath. It will also be possible to form the ports over the length which is greater than the non-linear region defined by the agitator 30. The agitator 30 is shown to be a short helical section having one complete turn. Other geometries will include two-dimensional geometries, such as single humps, S-shapes, zig-zag patterns, and the like. Suitable three-dimensional geometries include helical geometries, alternating helixes, spirals, and the like. In all cases, as the non-linear region of the agitator is rotated within the sheath, the sheath will be caused to trace a three-dimensional envelope within the blood vessel being treated. Usually, the agitator 30 will force the sheath into engagement with clot or thrombus within the blood vessel, and the thrombolytic agent will be released through the ports 40 as the sheath is being engaged by the agitator. In this way, the thrombolytic agent is introduced directly into the clot or thrombus as the clot is being mechanically disrupted. This combination of mechanical and chemical dissolution of the clot is every effective and can reduce the clot disruption time significantly when compared to other thrombolytic techniques.

Figure 3:
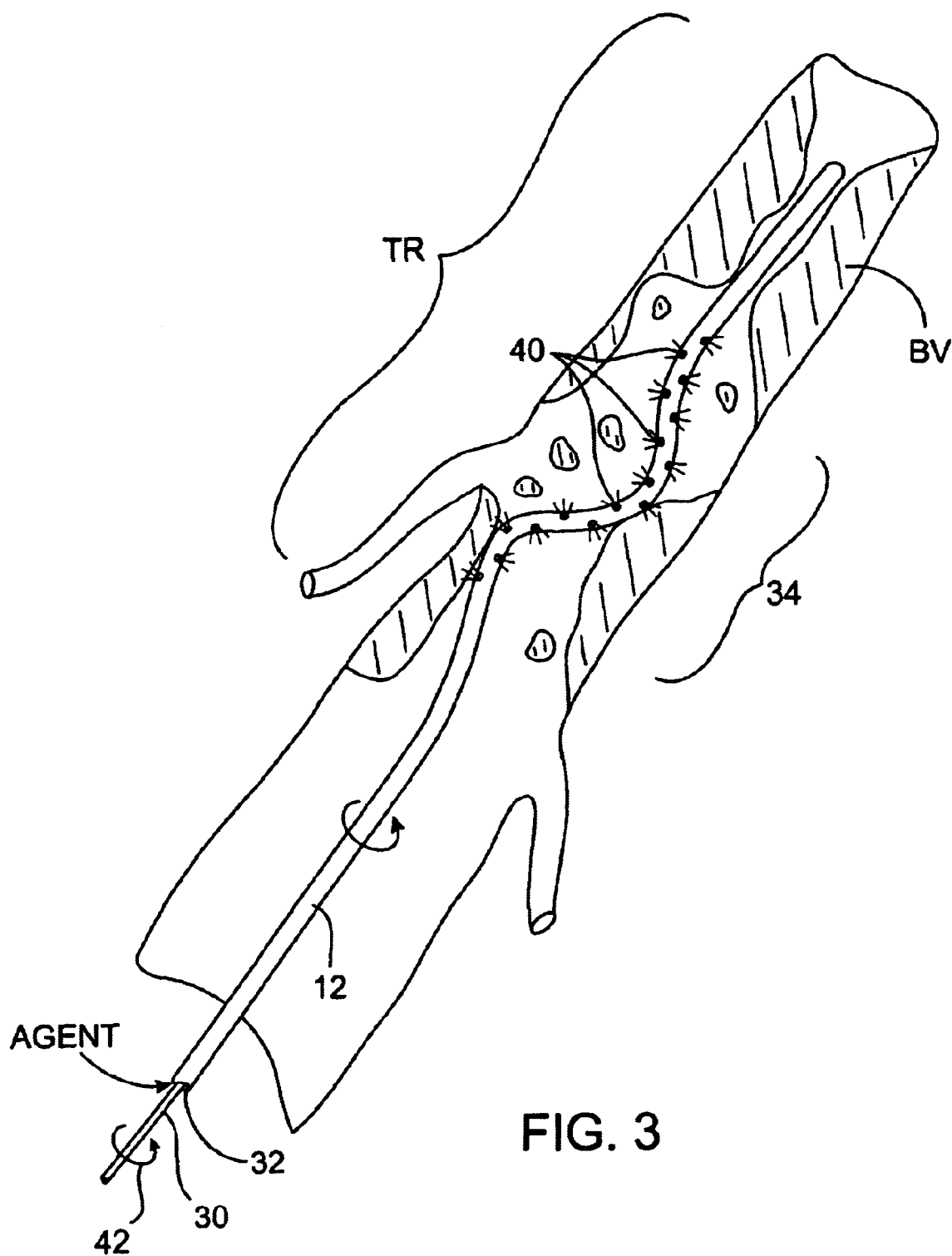
FIG. 3 illustrates use of the clot disruption apparatus of FIG. 1 in treating a thrombosed region within a blood vessel according to the methods of the present invention.

Use of the clot disruption apparatus 10 of FIGS. 1 and 2 is illustrated in FIG. 3. The non-linear region 34 of the catheter body 12 is positioned within a treatment region TR of the blood vessel BV being treated. Once in place, the agitator 30 is rotated, as indicated by arrow 42 and the non-linear region sweeps an ovoid volume within the treatment region TR, disrupting and dissolving clot as the thrombolytic agent is released from the ports 40. Alternatively or additionally, the non-linear region 34 could be rotated in the direction opposite to arrow 42, could be rotationally oscillated, axially oscillated, or combinations thereof.

Figure 4:
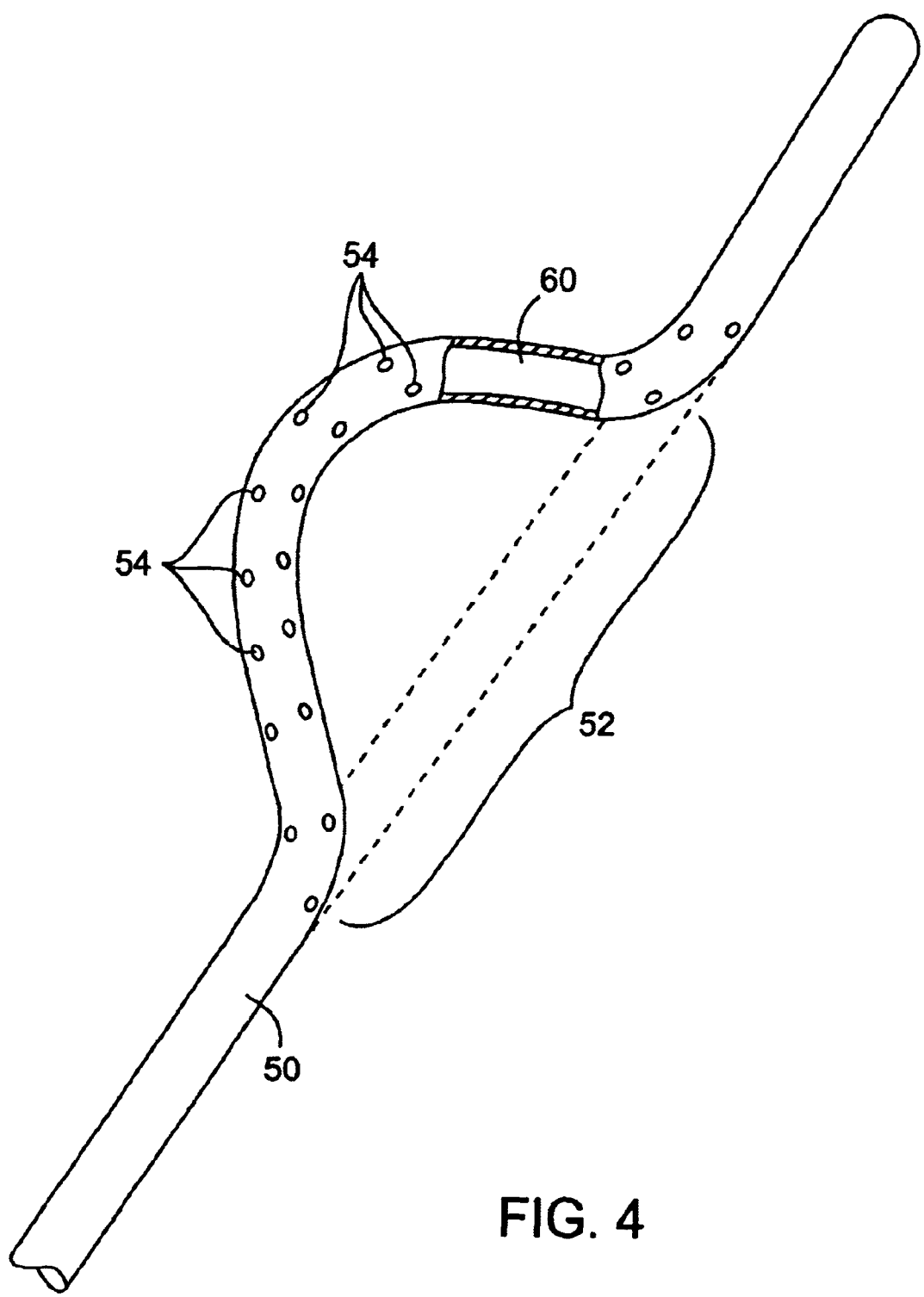
FIG. 4 illustrates an alternative construction of an agitator useful in the apparatus of the present invention.
Figure 5:
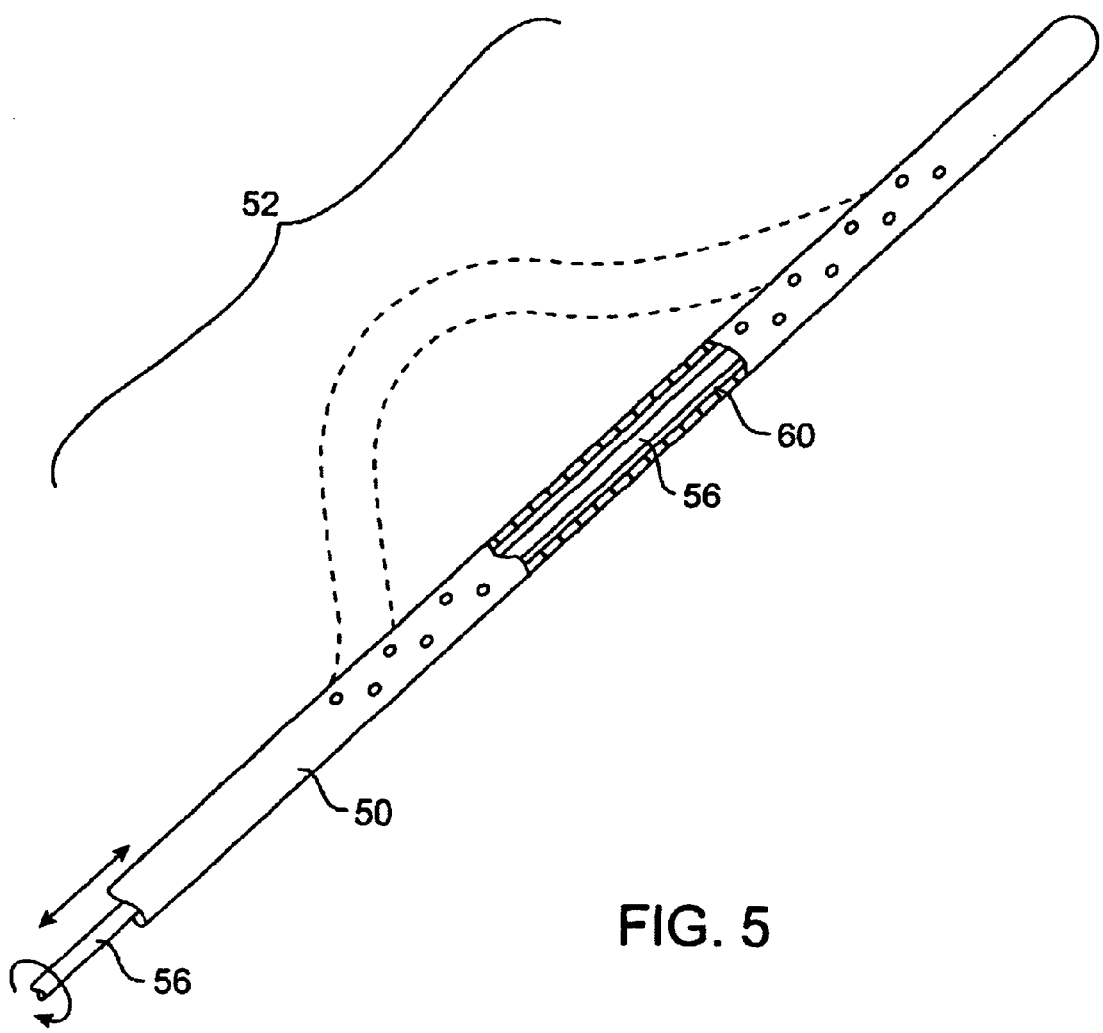
FIG. 5 illustrates a second alternative construction of an agitator useful in the apparatus of the present invention.

As described in the Summary above, the agitator may operate together with a thrombolytic agent delivery sheath (as illustrated in FIGS. 1–3) or may alternatively be configured to deliver the thrombolytic agent directly, e.g., through a lumen in the agitator as illustrated in FIG. 4. Agitator 50 of FIG. 4 includes a non-linear region 52 which consists of a simple, two-dimensional curve which forms a hump in the agitator. The non-linear region has a plurality of thrombolytic agent delivery ports 54 formed over its length so that the non-linear region 52 can release the thrombolytic agent directly into the thrombus being treated as the agitator is rotated. In a first instance, the agitator 50 may be formed from a resilient material with the non-linear curve being formed so that it assumes the curve when released from constraint. The agitator 50 could then be delivered to a target site within a blood vessel within a separate delivery sheath. When the agitator 50 is advanced from the sheath, it will assume the non-linear geometry illustrated in FIG. 4. Alternatively, as shown in FIG. 5, the sheath 50 can be delivered with an internal stiffener 56 which tensions the agitator so that the non-linear region 52 (shown in broken line) is straightened (shown in full line) when the stiffener 56 is axially advanced within the lumen 60 thereof. It will also be possible to configure the agitator 50 so that it assumes a straight configuration when free from axial tension and compression. When under compression, however, the agitator will be formed so that it will collapse and assume the non-linear configuration 52 shown in FIG. 4. The agitator 50 could also be formed from heat memory alloys which are straight at room temperature but which assume their non-linear configuration when introduced to the body temperature. By introducing such catheters in a cooled environment, e.g., while bathed in cooled saline, they can reach their target site in a straightened configuration and thereafter assume the non-linear configuration as they return to body temperature.

Figure 6:
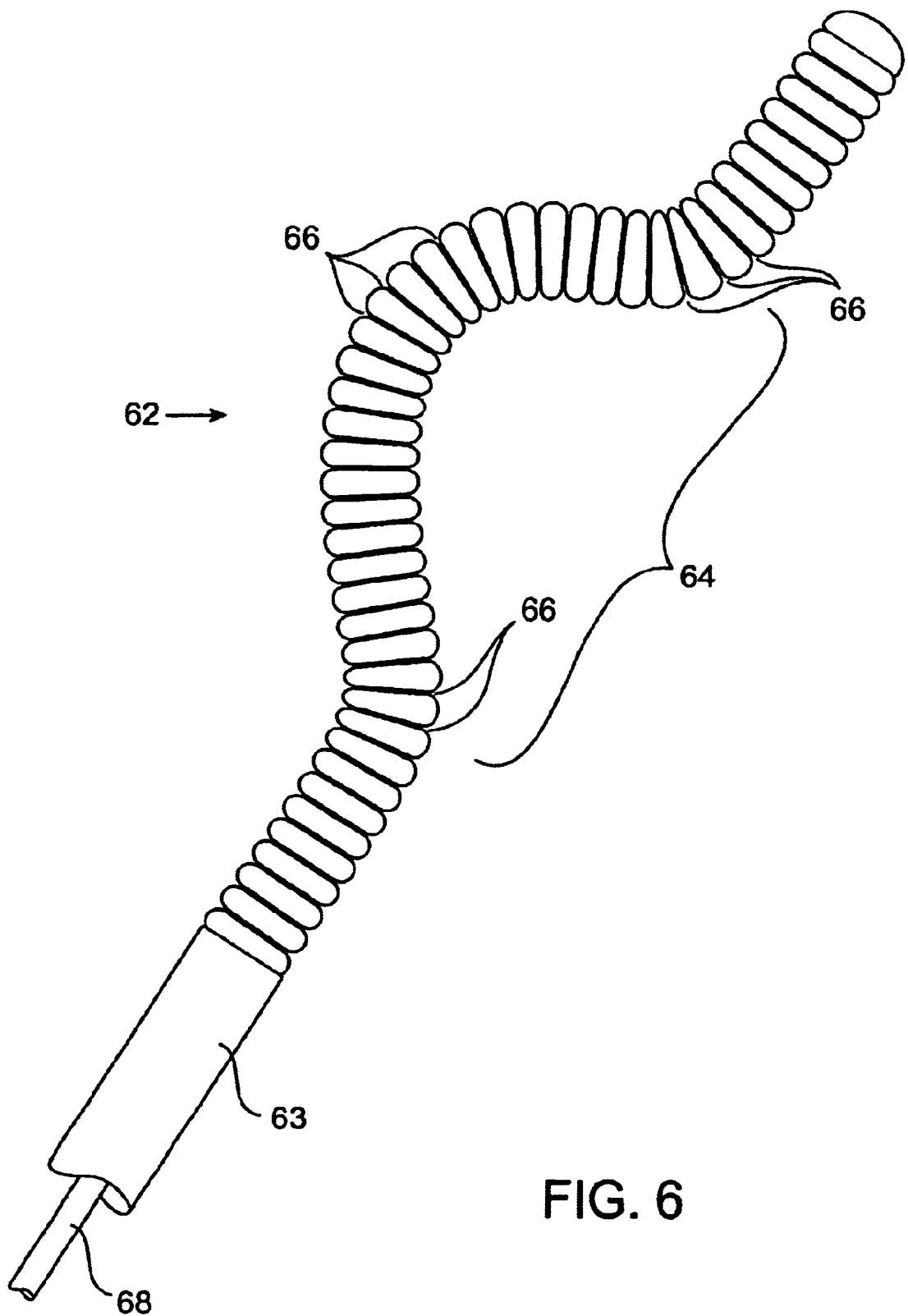
FIG. 6 illustrates a third alternative construction of an agitator useful in the apparatus of the present invention.

In addition to perforate structures for release of the thrombolytic agent, as shown in FIGS. 4 and 5, an agitator 62 having a sheath 63 formed as a coiled structure 64, as shown in FIG. 6, may also be used. The coil can be configured to have a non-linear region 64, such as a simple curve, or any of the other geometries discussed and illustrated above. When in a linear configuration, adjacent turns of the coil will lie close together and form a generally fluid-tight seal. When in the non-linear configuration illustrated in FIG. 6, however, adjacent turns of the coil will move apart to form a plurality of spaces or gaps 66 at regions where the coil structure turns. These gaps 66 connect to release the thrombolytic agent as the agitator is rotated. Sheath 63 may be induced into its linear configuration using a stiffening member 68, as illustrated.

Figure 7:
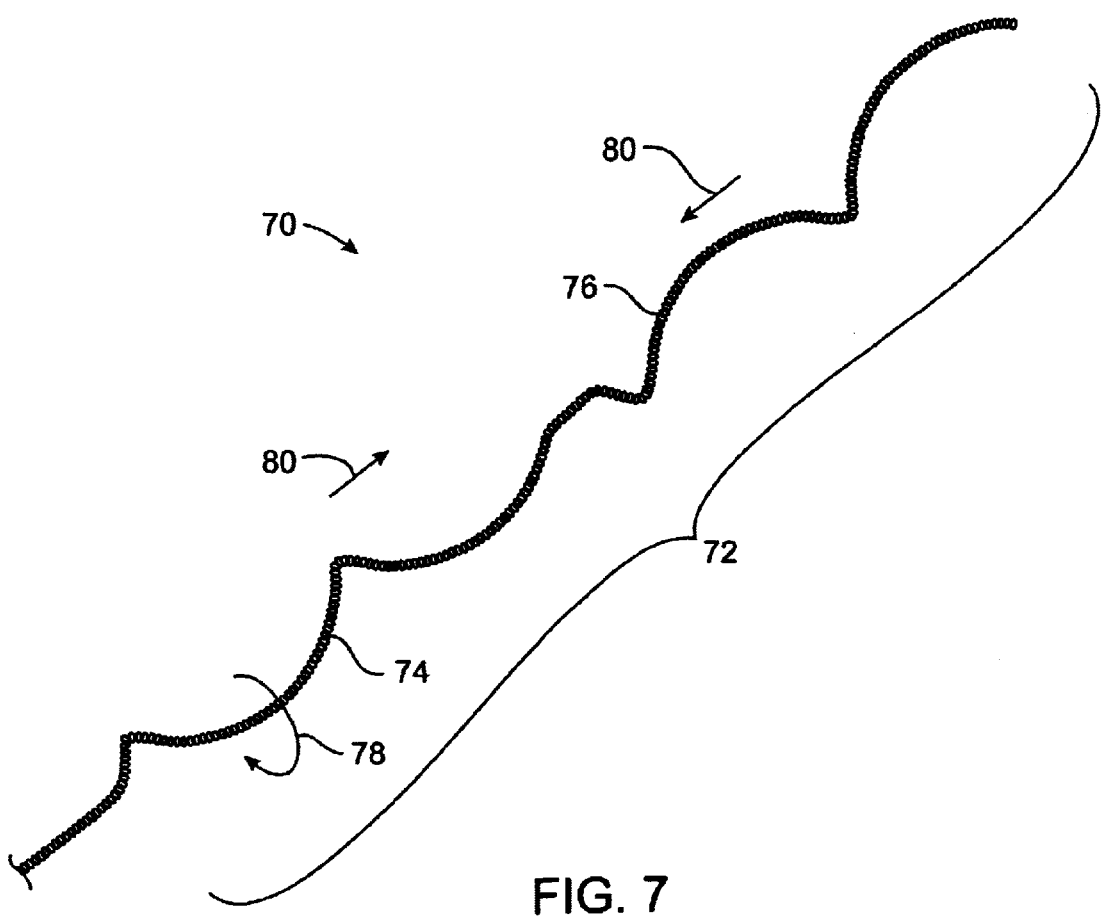
FIG. 7 illustrates a fourth configuration of an agitator useful in the apparatus of the present invention.

An agitator 70 having an alternating helical geometry is illustrated in FIG. 7. Non-linear region 72 of the agitator 70 comprises a first helical section 74 and a second helical section 76. The helical section 74 and 76 are wound in opposite directions so that when the agitator 70 is rotated in the direction of arrow 78, materials within the blood vessel lumen will be urged to move in the direction of arrows 80 toward a central region of the agitator 70. In this way, the agitator 70 creates its own isolation region within the blood vessel. The materials being disrupted and dissolved are constantly urged toward the center, to inhibit release from the treatment region. Over time, the materials will become completely broken down, or at least sufficiently broken down so that their release will not present significant risk to the patient.

Agitator 70 can comprise a sheath and separate agitator (similar to the design of FIGS. 1–3) or may comprise a monolithic structure where the thrombolytic agent is released directly through perforations or other discontinuities in the agitator wall.

Figure 8:
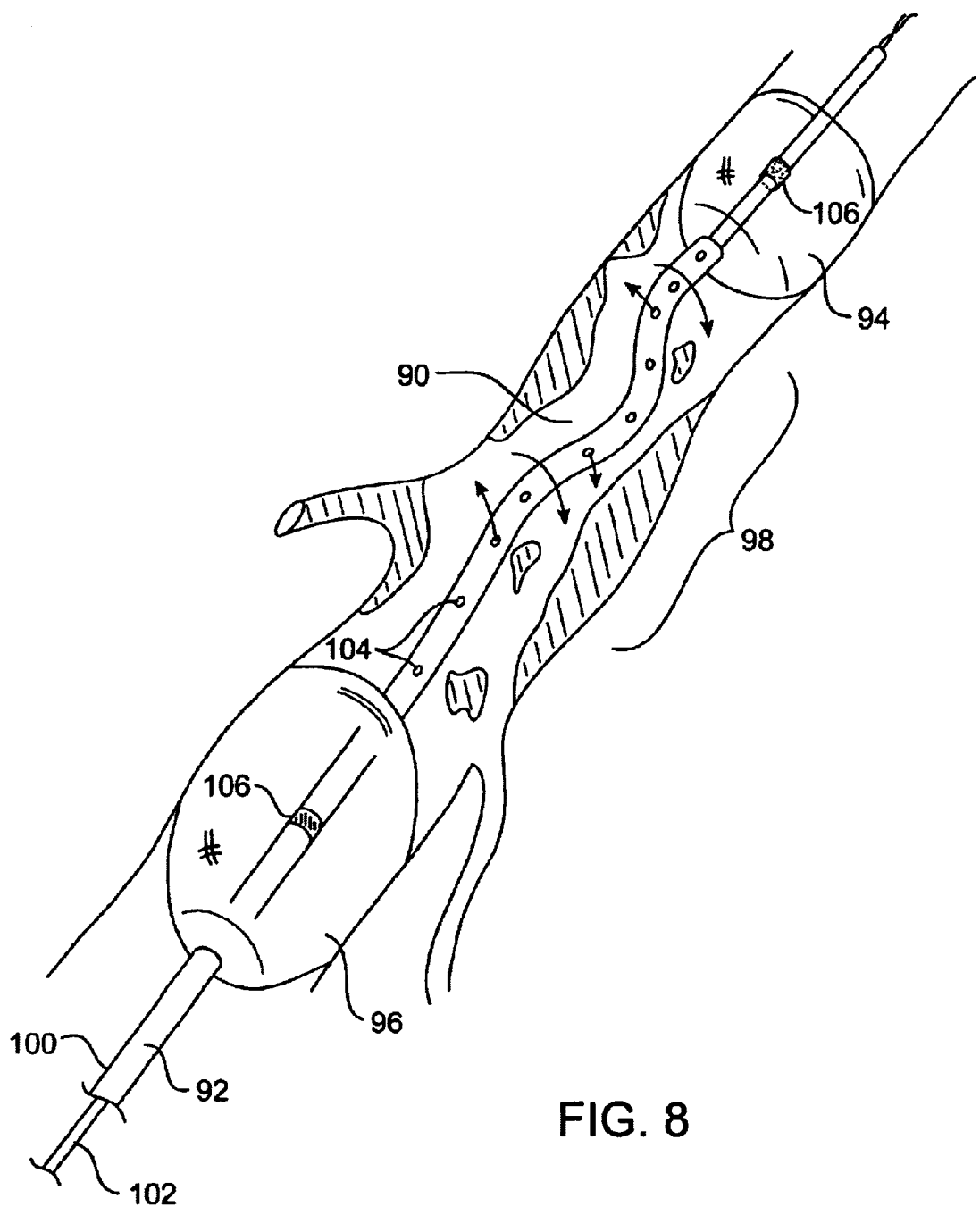
FIG. 8 illustrates a method and apparatus according to the present invention for treating an isolated region of the vasculature.

Referring now to FIG. 8, the clock disruption catheters of the present invention may be advantageously combined with balloon or other isolation means. Clot disruption catheter 90 comprises a catheter body 92 having a distal isolation balloon 94 and proximal isolation balloon 96 formed thereon. A non-linear region 98 of the catheter body 92 is formed between the isolation balloons 94 and 96. Conveniently, the isolation balloons 94 and 96 may be formed directly over a sheath 100 which remains stationary while an agitator 102 is rotated, oscillated, and/or axially translated therein. The balloons 94 and 96 may be inflated through a common or separate inflation lumens formed within the sheath 92. The inflation lumens (not shown) will be isolated from the thrombolytic agent delivery lumen. Thrombolytic agent is delivered through ports 104 formed in the sheath between the isolation balloons 94 and 96. Radiopaque markers 106 are positioned at either end of the treatment region, typically within the isolation balloons 94 and 96. The structure of catheter 90 is advantageous in that it will completely contain the thrombolytic agent and all disrupted clot between the isolation balloons 94 and 96. Optionally, aspiration means can be provided, e.g., through a fourth lumen within the sheath 100, in order to withdraw materials from the treatment region.

Figure 9:
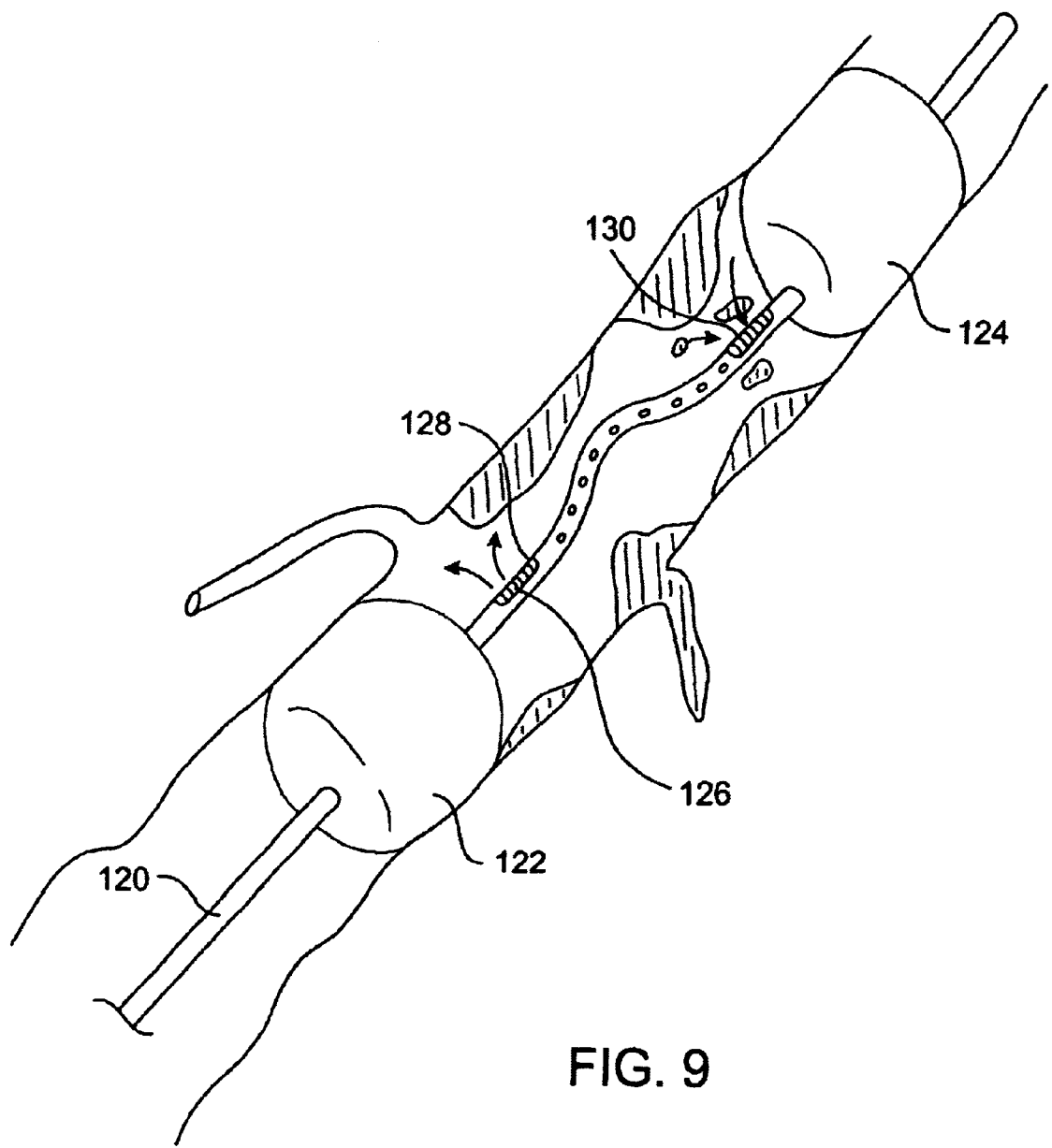
FIGS. 9, 9A and 9B illustrate alternative methods and apparatus according to the present invention for treating an isolated region of the vasculature.

Referring now to FIG. 9, a catheter 120 having means for recirculating the thrombolytic agent and other materials through a treatment region is illustrated. Catheter 120 comprises spaced-apart isolation balloons 122 and 124. The catheter is generally similar to that described above with reference to FIG. 8. Catheter 120, however, further includes a pump, typically in the form of an Archimedes screw 126 disposed between a first port 128 and a second port 130 on the body of catheter 120. Rotation of the Archimedes screw will draw material into the port 130 and expel the material from port 128. Such recirculation enhances the agitation and thrombolytic activity of the thrombolytic agent which is released through the ports as generally described above with respect to all earlier embodiments.

Figure 9A:
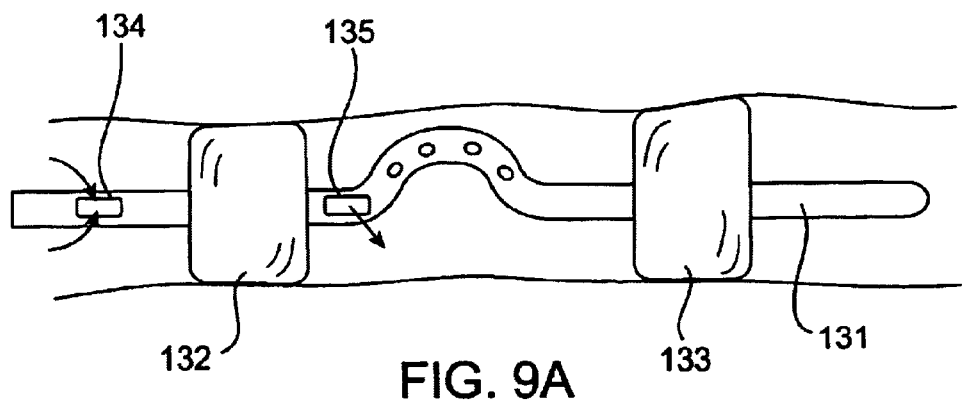

The catheters of the present invention can also be provided with blood bypass and perfusion lumens for a variety of purposes. For example, as illustrated in FIG. 9A, a catheter 131 having spaced-apart balloons 132 and 133 can have an inlet port upstream of proximal balloon 132 and an outlet port 135 between the balloons 132 and 133. In this way, fresh blood can be introduced into the otherwise isolated region between the balloons to enhance the thrombolytic activity of the tPA or other thrombolytic agent being released by the catheter.

Figure 9B:
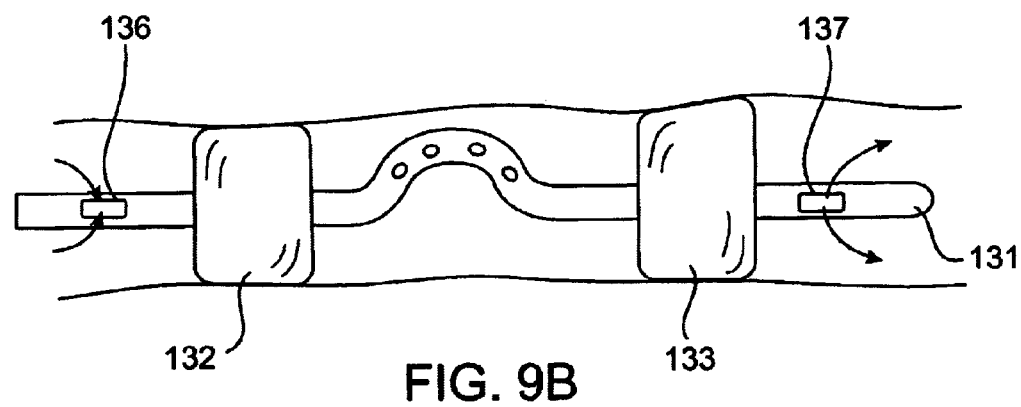

As illustrated in FIG. 9B, catheter 131 could also be provided with an inlet port 136 upstream of proximal balloon 132 and an outlet port 137 downstream of distal balloon 133 in order to provide perfusion downstream of the region being treated. In both FIGS. 9A and 9B, the inlet and outlet ports will be connected by internal lumen(s) which are preferably isolated from the lumen(s) which are supplying the thrombolytic agent.

Figure 10A:
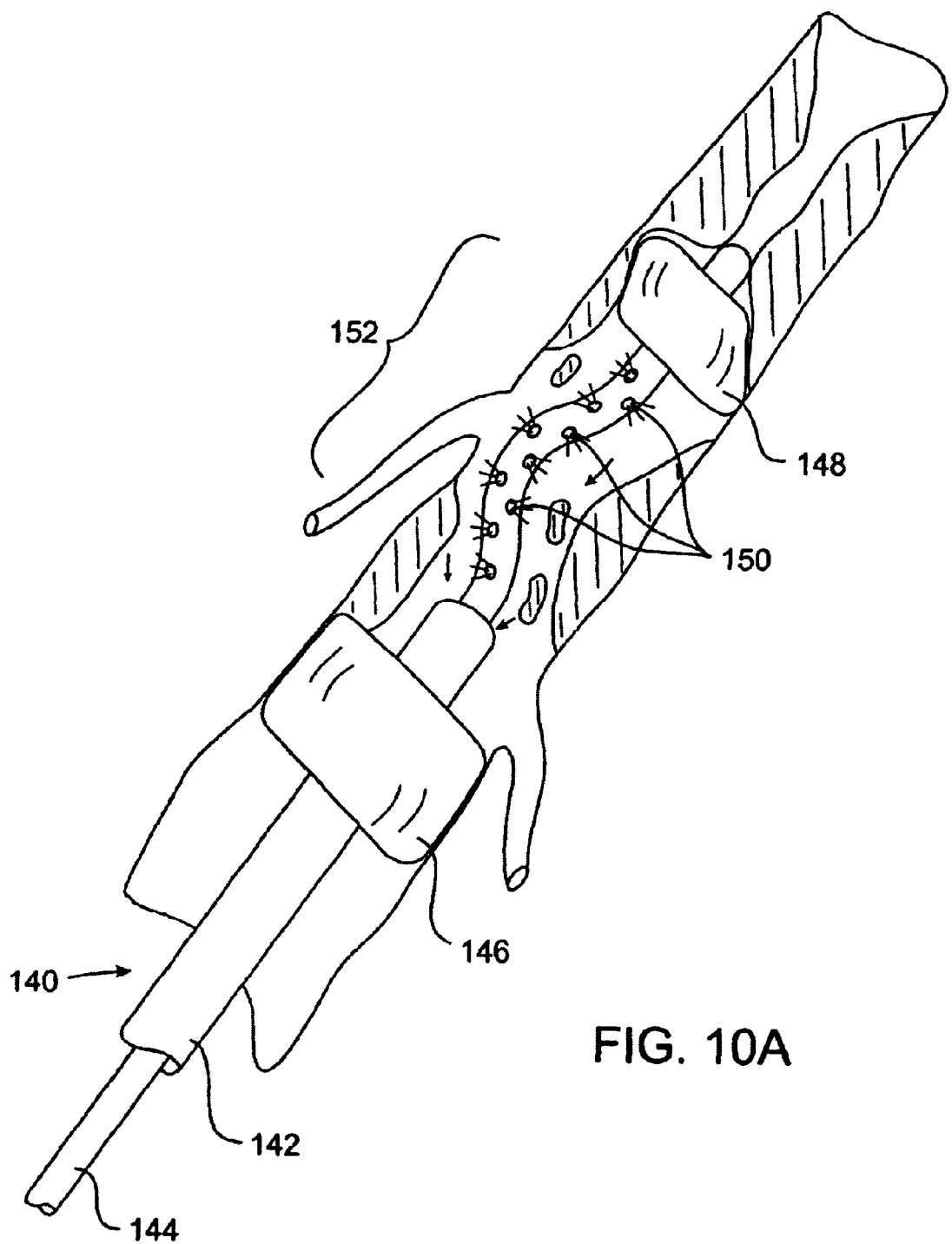
FIGS. 10A and 10B illustrate yet another alternative embodiment of the methods and apparatus of the present invention for treating an isolated region of the vasculature.
Figure 10B:
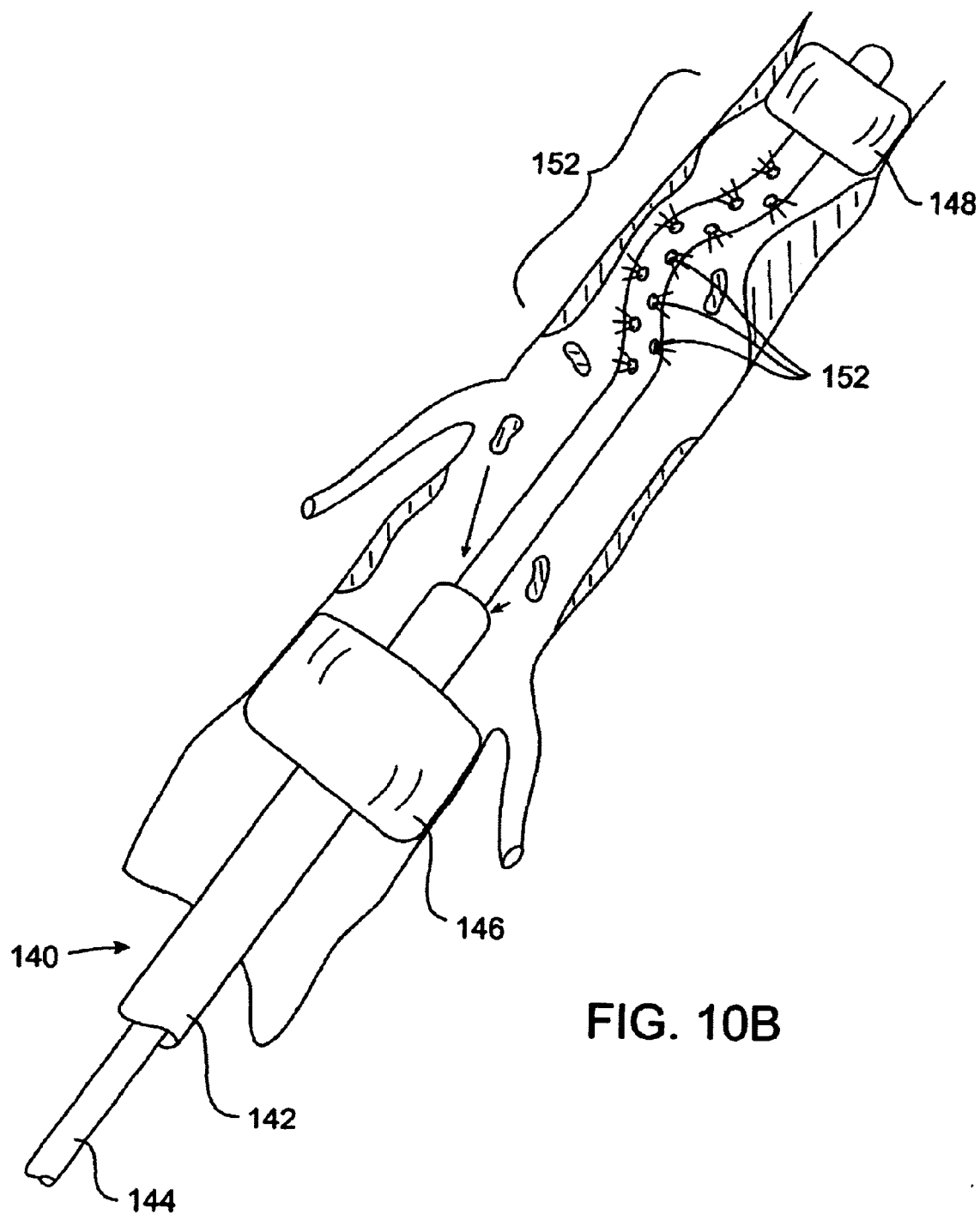

FIGS. 10A and 10B illustrate a catheter 140 comprising catheter body 142 and an inner catheter shaft 144. A proximal isolation balloon 146 is formed at the distal end of the catheter body 142. The distal isolation balloon 148 is formed at the distal end of the inner catheter body 144. Thrombolytic agent distribution ports 150 are formed over a non-linear region 152 of the inner catheter body 144. In this way, the length of the non-linear region and thrombolytic agent release region 152 can be adjusted by axially extending or retracting the inner catheter member 144 relative to the catheter body 142. In particular, balloon 146 on catheter body 142 may be anchored at a proximal end of a desired treatment region. The distal isolation balloon 148 may then be extended by a desired distance from the distal tip of the catheter body 142 to create an isolated treatment region therebetween (with both balloons being inflated). The non-linear region 152 may then be rotated with thrombolytic agent released in order to treat the clot and thrombus between the balloons. Optionally, the released emboli can be aspirated through the distal end of the catheter body 142 and withdrawn from the treatment region. After a first portion of the treatment region is remediated, the distal isolation balloon 148 can be deflated, and the distal end of the inner catheter member 144 extended further distally. This creates a new treatment region, which region can be treated in the manner just described, Two, three, or more such iterations can be performed successively in order to treat disseminated disease within a blood vessel lumen.

Figure 11:
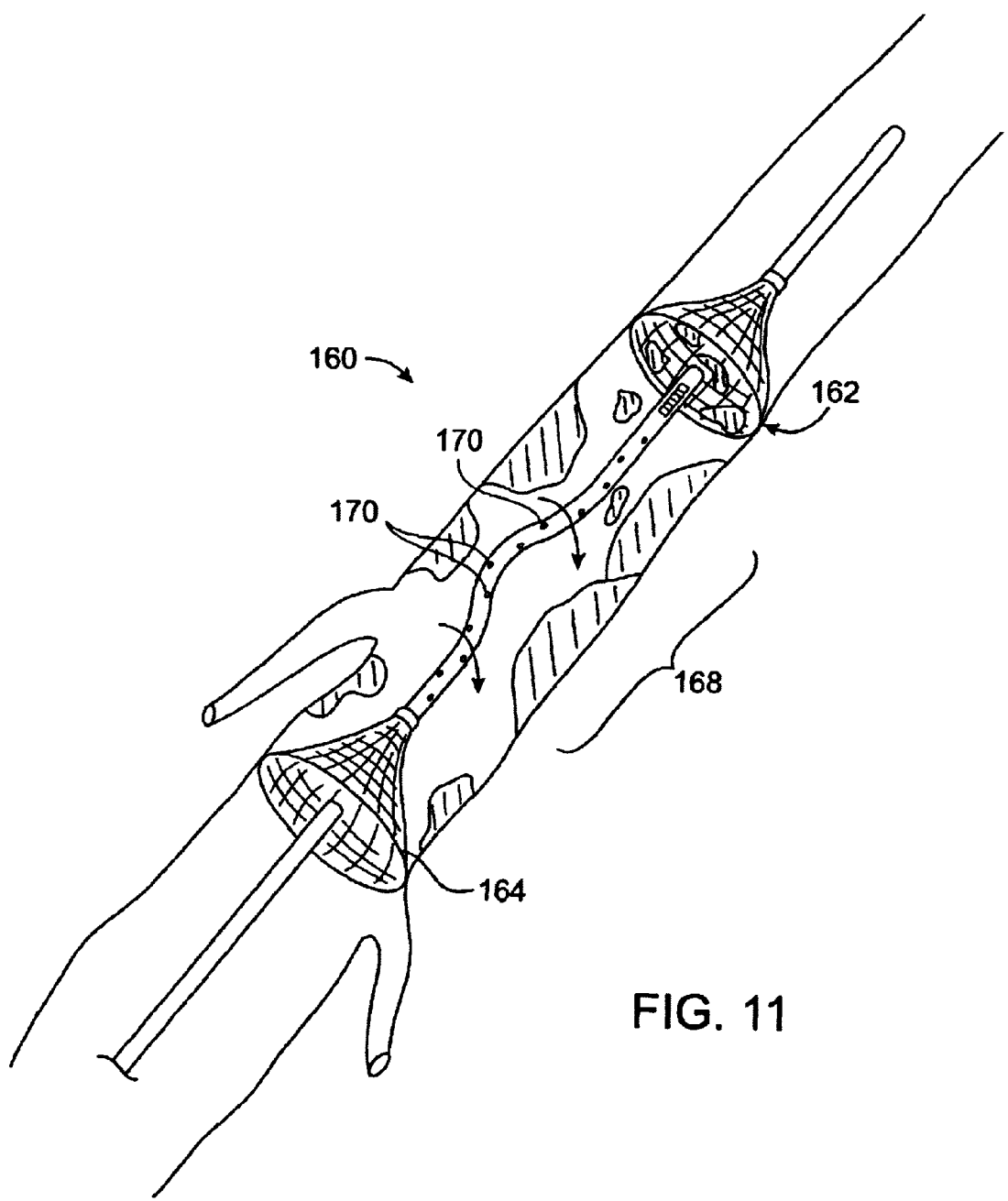
FIG. 11 illustrates a still further embodiment of the apparatus and methods of the present invention for treating an isolated region of the vasculature.

Referring now to FIG. 11, a clot disruption catheter 160 comprising expansible filter elements 162 and 164 is illustrated. The filter elements 162 and 164 provide partial isolation of a treatment region therebetween. The filter elements will capture emboli, but generally permit blood flow through the region. Catheter 160 further includes a non-linear region 168 and thrombolytic agent delivery ports 170, generally as described for previous embodiments. The non-linear region 168 may be rotated in order to effect clot disruption and dissolution, again generally as described above. Filter elements 162 and 164 will serve to capture at least most of the clot which is released.

Figure 12:
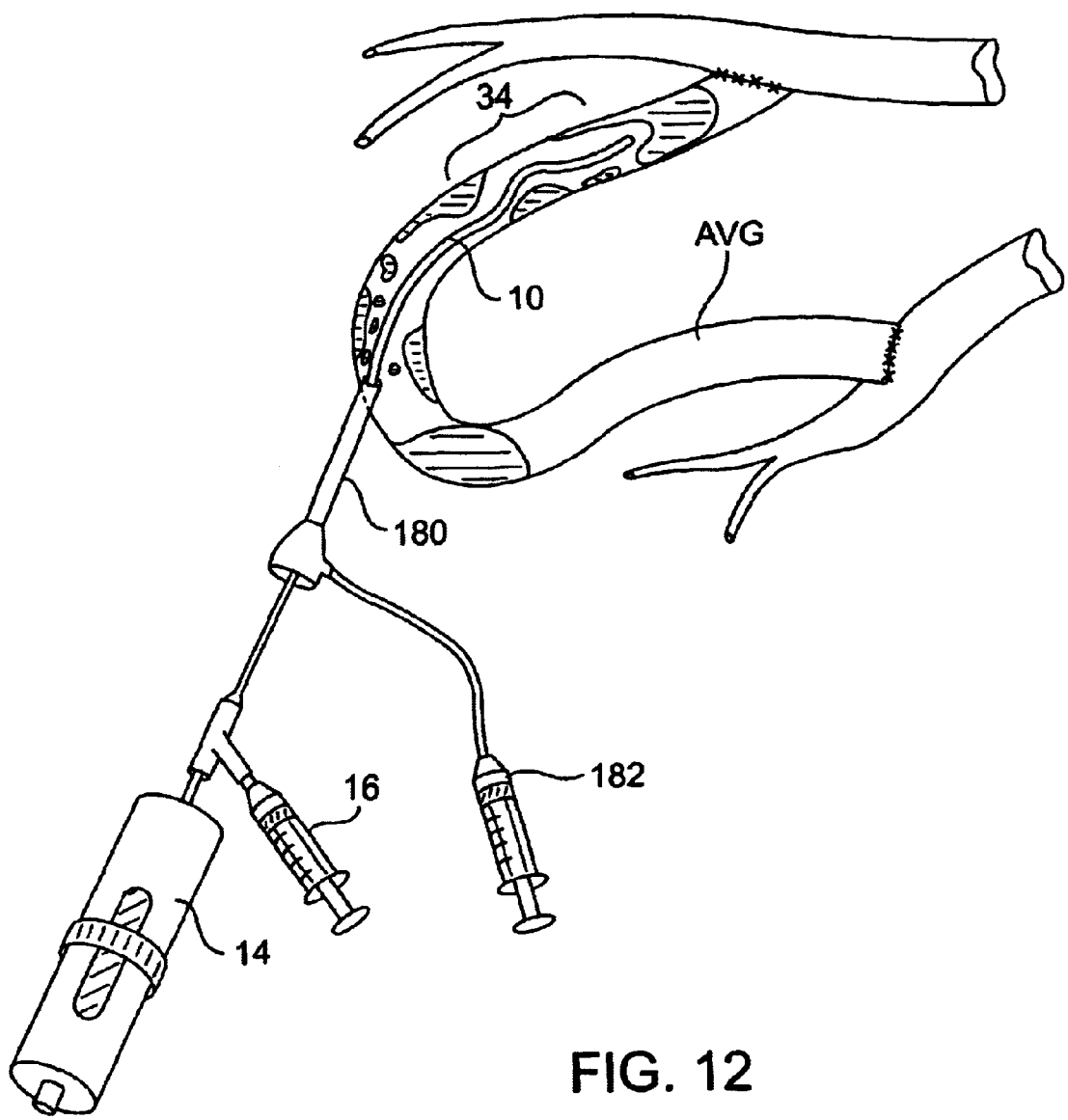
FIG. 12 illustrates a first method for treating an arterio-venous graft according to the methods of the present invention.

Referring now to FIG. 12, a clot disruption catheter, such as catheter 10 may be used to treat an arterio-venous graft AVG. The catheter 10 is introduced through a delivery sheath 180 so that non-linear region 34 lies within a highly thrombosed region of the graft AVG. The catheter is rotated and optionally axially translated, generally as described above. Thrombolytic agent can be released through the delivery device 16. The delivery sheath 180 can be adapted to provide for aspiration through a syringe 182 in order to retrieve at least a portion of the clot which is released from the graft.

Figure 13:
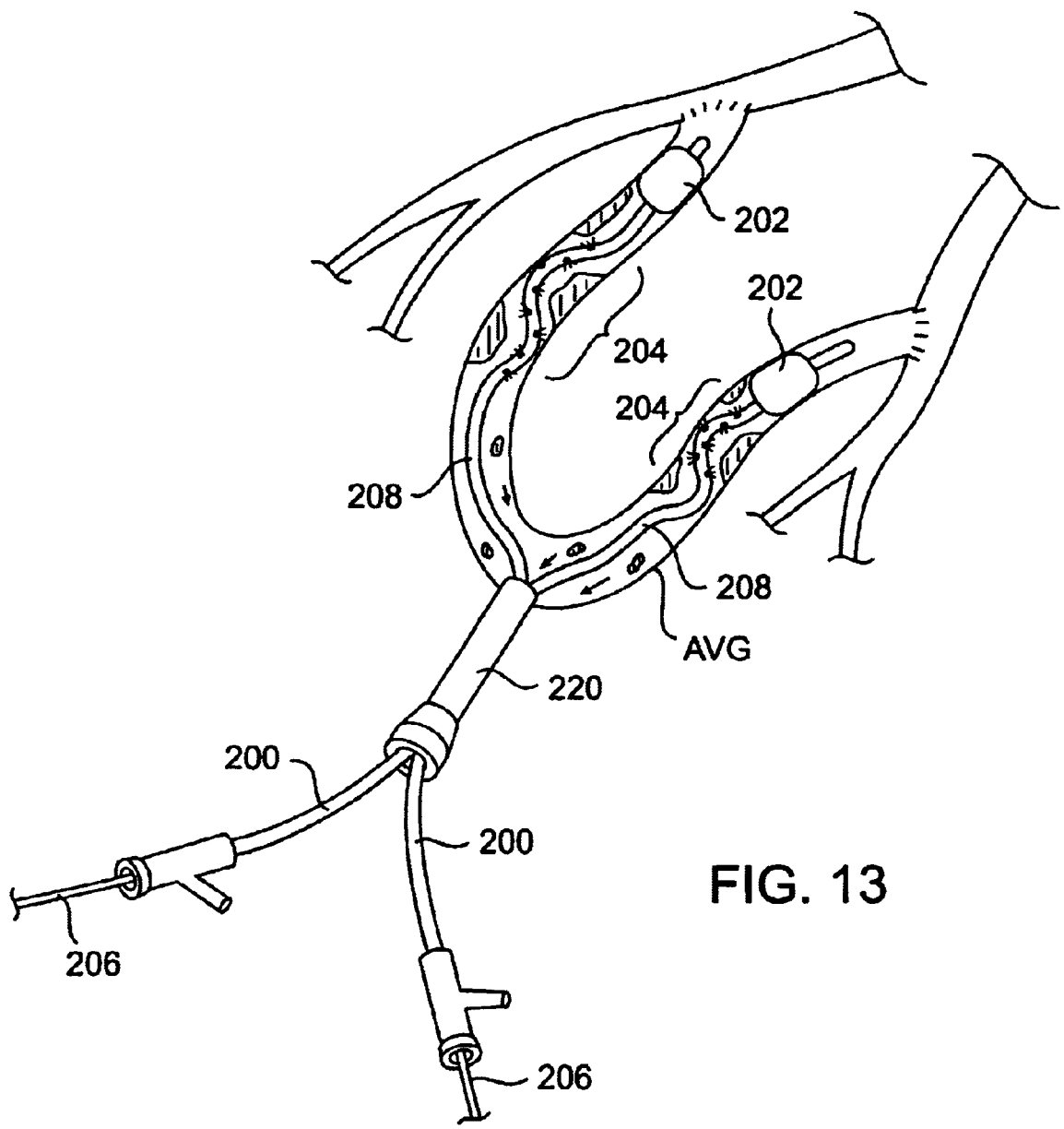
FIG. 13 illustrates a second method employing a pair of clot disruption catheters for treating an arterio-venous graft according to the methods of the present invention.

Two or more of the clot disruption catheters of the present invention may be used at the same time to treat a diseased region (or more than one diseased regions) within the patient. Referring to FIG. 13, an arterio-venous graft AVG can be treated with a pair of identical catheters 200, each of which includes a distal isolation balloon 202 but which does not include any proximal or other isolation balloons. Each catheter 200 further includes a non-linear region 204 defined by an agitator 206 within an exterior sheath 208. The AVG can be treated by positioning each distal isolation balloon 202 at a position close to the anastomotic junction with the associated artery and vein. The catheters 200 are introduced through a common delivery sheath 220, and the agitators 206 may be axially translated (repositioned) within the sheath in order to treat substantially the entire length between the distal isolation balloon 202 and the delivery sheath 220. Thrombolytic agent will be delivered generally as described above in other embodiments. Similarly, the non-linear regions 204 will be rotated in order to effect clot disruption and enhance thrombolytic agent activity. After treatment is completed, both catheters may be withdrawn through the sheath 220 and the AVG graft closed in the conventional manner.

Figure 14:
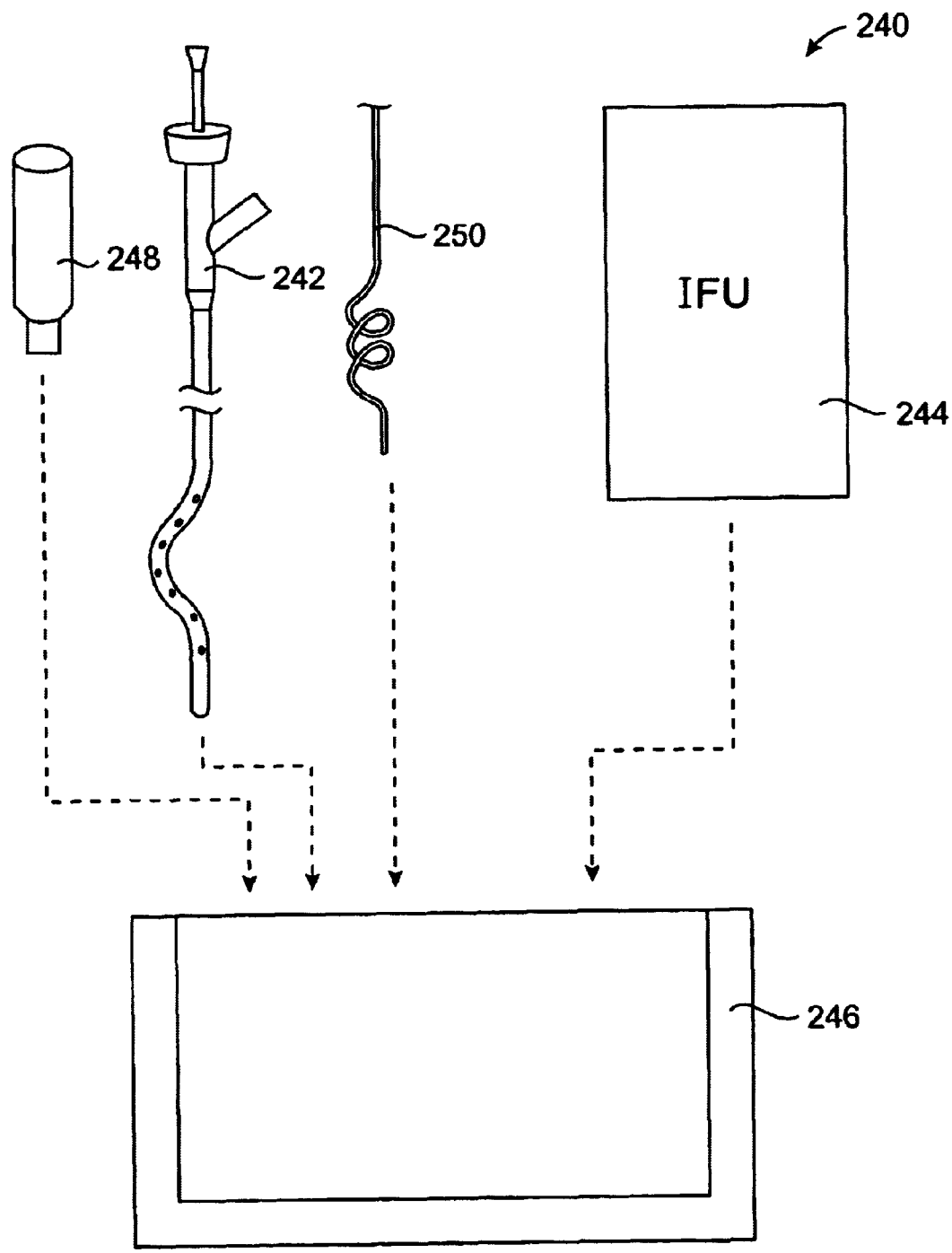
FIG. 14 illustrates a kit for performing the methods of the present invention, wherein the kit is constructed in accordance with the principles of the present invention.

The present invention still further comprises kits including at least some of the system components of the apparatus of the present invention described herein together with packaging, instructions for use, and/or other conventional kit components. For example, as illustrated in FIG. 14, a kit 240 may comprise at least a catheter 242, instructions for use 244, and packaging 246. The catheter 242 can be any of the catheters described hereinabove, and the instructions for use 244 may set forth any of the methods of the present invention described hereinabove. The catheter 242 will be packaged within the packaging 246, typically in a sterile fashion. Conventional medical device packaging may be used, such as a pouch, tube, tray, box, or the like. The instructions for use may be printed on a separate package insert, or may be printed in whole or in part on the packaging. Other kit components, such as a motor drive unit 248, an additional agitator 250 (optionally including two or more additional agitators having different geometries), may also be added.

While the above is a complete description of the preferred embodiments of the invention, various alternatives, modifications, and equivalents may be used. Therefore, the above description should not be taken as limiting the scope of the invention which is defined by the appended claims.

What is claimed is:

1. Apparatus for disrupting clot over a predetermined luminal length of a blood vessel, said apparatus comprising:
   a catheter body having a proximal end and a distal end;
   means near the distal end of the catheter body for agitating clot over the predetermined length in the blood vessel, the agitating means extending along a length of the catheter body;
   means near the distal end of the catheter body for distributing an agent over the predetermined length in the blood vessel, wherein the agent distributing means is disposed along the length of the catheter body; and
   means for aspirating disrupted clot from a region around the mechanical agitation means.

2. Apparatus as in claim 1, wherein the agitating means comprises a rotatable and/or axially translatable agitator.

3. Apparatus as in claim 2, wherein the agitator comprises a resilient element which may be radially constrained to have a low profile or may be freed from radial constraint to have an enlarged profile having a non-linear geometry.

4. Apparatus as in claim 2, wherein the agitator comprises a resilient element which may be axially shortened to assume an enlarged profile having a non-linear geometry.

5. Apparatus as in claim 3 or 4, wherein the resilient element has a non-linear geometry selected from the group consisting of helical, spiral, serpentine, zig-zag, alternating helical, and random.

6. Apparatus as in claim 1, wherein the agitating means comprises mechanical agitating means.

7. Apparatus as in claim 6, wherein the mechanical agitating means agitates at a frequency of about 10–20,000 Hz.

8. Apparatus as in claim 1, wherein the agent is a member selected from the group consisting of a thrombolytic agent, a fibrinolytic agent, a calcium dissolving agent, a gene therapy agent, an anti-reproliferative agent, and a group GP IIb/IIIa Inhibitor.

9. Apparatus for disrupting clot over a predetermined luminal length of a blood vessel, said apparatus comprising:
   a catheter body having a proximal end and a distal end;
   means near the distal end of the catheter body for mechanically agitating clot over the predetermined length in the blood vessel, the mechanical agitating means comprising a rotatable and/or axially translatable agitator comprising a resilient element which may be radially constrained to have a low profile or may be freed from radial constraint to have an enlarged profile having a non-linear geometry selected from the group consisting of helical, spiral, serpentine, zig-zag, alternating helical, and random; and
   means near the distal end of the catheter body for distributing a thrombolytic agent over the predetermined length in the blood vessel, the thrombolytic distributing means comprising a porous sheath disposed over the resilient element.

10. Apparatus as in claim 9, wherein the porous sheath is flexible and wherein the resilient element presses the sheath into the clot.

11. Apparatus as in claim 9, wherein the thrombolytic distributing means comprises a distribution element in the resilient element, wherein the resilient element includes means for infusing the thrombolytic agent disposed over its length.

12. Apparatus as in claim 11, wherein the infusing means comprises a plurality of spaced-apart ports.

13. Apparatus for disrupting clot over a predetermined luminal length of a blood vessel, said apparatus comprising:
   a catheter body having a proximal end and a distal end;
   means near the distal end of the catheter body for mechanically agitating clot over the predetermined length in the blood vessel, the mechanical agitating means comprising a rotatable and/or axially translatable agitator comprising a resilient element which may be radially constrained to have a low profile or may be freed from radial constraint to have an enlarged profile having a non-linear geometry selected from the group consisting of helical, spiral, serpentine, zig-zag, alternating helical, and random; and
   means near the distal end of the catheter body for distributing a thrombolytic agent over the predetermined-length in the blood vessel, the thrombolytic distributing means comprising a distribution element in the resilient element, the resilient element including means for infusing the thrombolytic agent disposed over its length, the infusing means comprising porous region(s) over the length of the resilient element.

14. Apparatus for disrupting clot over a predetermined luminal length of a blood vessel, said apparatus comprising:
   a catheter body having a proximal end and a distal end;
   means near the distal end of the catheter body for mechanically agitating clot over the predetermined length in the blood vessel; and
   means near the distal end of the catheter body for distributing a thrombolytic agent over the predetermined length in the blood vessel, the thrombolytic distributing means comprising a porous sheath disposed over the mechanical agitating means.

15. Apparatus as in claim 14, wherein the porous sheath is flexible and wherein the mechanical agitating means presses the sheath into the clot.

16. Apparatus for disrupting clot over a predetermined luminal length of a blood vessel, said apparatus comprising:
   a catheter body having a proximal end and a distal end;
   means near the distal end of the catheter body for mechanically agitating clot over the predetermined length in the blood vessel;
   means near the distal end of the catheter body for distributing a thrombolytic agent over the predetermined length in the blood vessel; and means for isolating at least one location on the catheter body to reduce blood flow through a region in a blood vessel being treated.

17. Apparatus as in claim 16, wherein the isolating means isolates both a proximal end and the distal end of the region being treated.

18. Apparatus as in claim 17, wherein the isolating means comprises a pair of axially spaced-apart balloons on the catheter body.

19. Apparatus as in claim 16, 17, or 18, further comprising means for aspirating disrupted clot from a region around the mechanical agitation means.

20. Apparatus for disrupting clot over a predetermined luminal length of a blood vessel, said apparatus comprising:
   a catheter body having a proximal end and a distal end;
   means near the distal end of the catheter body for mechanically agitating clot over the predetermined length in the blood vessel, the mechanical agitating means comprising a rotatable and/or axially translatable agitator comprising a resilient element which may be axially shortened to assume an enlarged profile having a non-linear geometry selected from the group consisting of helical, spiral, serpentine, zig-zag, alternating helical, and random; and
   means near the distal end of the catheter body for distributing a thrombolytic agent over the predetermined length in the blood vessel, the thrombolytic distributing means comprising a porous sheath disposed over the resilient element.

21. Apparatus for disrupting clot over a predetermined luminal length of a blood vessel, said apparatus comprising:
   a catheter body having a proximal end and a distal end;
   means near the distal end of the catheter body for mechanically agitating clot over the predetermined length in the blood vessel, the mechanical agitating means comprising a rotatable and/or axially translatable agitator comprising a resilient element which may be axially shortened to assume an enlarged profile having a non-linear geometry selected from the group consisting of helical, spiral, serpentine, zig-zag, alternating helical, and random; and
   means near the distal end of the catheter body for distributing a thrombolytic agent over the predetermined length in the blood vessel, the thrombolytic distributing means comprising a distribution element in the resilient element, the resilient element including means for infusing the thrombolytic agent disposed over its length, the infusing means comprising porous region(s) over the length of the resilient element.

22. Apparatus for disrupting clot within a blood vessel, said apparatus comprising:
   a catheter body having a proximal end and a distal end;
   a first radially expandable body near the distal end of the catheter body, for inhibiting flow;
   a second radially expandable body proximal to the first radial expandable body, for inhibiting flow, wherein the first and second radially expandable bodies comprise filters;
   a mechanical agitator along the catheter body for mechanically agitating clot over a length of the blood vessel, the length of the blood vessel extending from adjacent the first radially expandable body to adjacent the second radially expandable body; and
   a thrombolytic distributor between the first and second radially expandable bodies, for distributing a thrombolytic agent over the length of the blood vessel.

23. Apparatus as in claim 22, wherein the thrombolytic distributor comprises a flexible, porous sheath disposed over the mechanical agitator, and the mechanical agitator presses the sheath into the clot.

24. Apparatus for disrupting clot within a blood vessel, said apparatus comprising:
   a catheter body having a proximal end and a distal end;
   a first radially expandable body near the distal end of the catheter body, for inhibiting flow;
   a second radially expandable body proximal to the first radial expandable body, for inhibiting flow;
   a mechanical agitator along the catheter body for mechanically agitating clot over a length of the blood vessel, the length of the blood vessel extending from adjacent the first radially expandable body to adjacent the second radially expandable body; and
   a thrombolytic distributor between the first and second radially expandable bodies, for distributing a thrombolytic agent over the length of the blood vessel, wherein the thrombolytic distributor comprises a flexible, porous sheath disposed over mechanical agitator, and the mechanical agitator presses the sheath into the clot.

25. Apparatus as in claim 24, wherein the first and second radially expandable bodies comprised balloons.

26. Apparatus as in claim 25, wherein the first and second radially expandable bodies comprise filters.

\* \* \* \* \*